(12) United States Patent
Cianciosi et al.

(10) Patent No.: US 6,482,952 B2
(45) Date of Patent: Nov. 19, 2002

(54) PROCESS FOR PREPARING ACETONIDES

(75) Inventors: Steven J. Cianciosi, Leesburg, GA (US); Gregory L. Tewalt, Lansdale, PA (US); Eric T. Pisk, Harrisonburg, VA (US); Ilia A. Zavialov, East Windsor, NJ (US); Glenn A. Hulvey, Harrisonburg, VA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/883,417

(22) Filed: Jun. 18, 2001

(65) Prior Publication Data

US 2002/0132837 A1 Sep. 19, 2002

Related U.S. Application Data

(60) Provisional application No. 60/212,759, filed on Jun. 20, 2000.

(51) Int. Cl.[7] .............................................. C07D 263/52
(52) U.S. Cl. ....................................................... 548/217
(58) Field of Search ......................................... 548/217

(56) References Cited

U.S. PATENT DOCUMENTS

| | | |
|---|---|---|
| 5,169,952 A | 12/1992 | Askin et al. |
| 5,413,999 A | 5/1995 | Vacca et al. |
| 5,491,238 A | 2/1996 | Askin et al. |
| 5,646,148 A | 7/1997 | Huff et al. |
| 5,728,840 A | 3/1998 | Askin et al. |

FOREIGN PATENT DOCUMENTS

WO    WO 97/47632    12/1997

OTHER PUBLICATIONS

D. Askin, "The synthesis of indinavir and other clinically useful HIV–1 protease inhibitors", Drug Discovery & Development, vol. 1, No. 3, pp. 338–348 (1998).

D. Askin et al., "Highly Diasteroeselective Alkylations of Chiral Amide Enolates: New Routes to Hydroxyethylene Dipeptide Isostere Inhibitors of HIV–1 Protease", J. Org.Chem., vol. 52, pp. 2771–2773 (1992) [includes supplementary material].

*Primary Examiner*—Joseph K. McKane
*Assistant Examiner*—Andrea D. Small
(74) *Attorney, Agent, or Firm*—Kenneth R. Walton; Melvin Winokur

(57) ABSTRACT

Acetonides are obtained in a one-step reaction of a carboxylic acid halide, a 1,2-aminoalcohol, and 2-alkoxypropene or 2,2-dialkoxypropane in an ether solvent and in the presence of an inorganic base. Acetonides are also obtained in a two-step reaction scheme in which an acid halide and 1,2-aminoalcohol are reacted in an ether solvent in the presence of LiOH to form a hydroxyamide, which is then reacted with 2-alkoxypropene or 2,2-dialkoxypropane in the presence of acid to form the acetonide. The acetonides resulting from the one-step and two-step protocols can be further reacted with an allylating agent such as an allyl halide in the presence of a strong base to provide the corresponding allyl acetonide. The acetonides and allyl acetonides can serve as intermediates in the production of certain HIV protease inhibitors which are useful for treating HIV infection and AIDS.

50 Claims, No Drawings

US 6,482,952 B2

1

PROCESS FOR PREPARING ACETONIDES

This application claims benefit of Ser. No. 60/212,759 Jun. 20, 2000.

FIELD OF THE INVENTION

The present invention relates to the preparation of 2,2-dimethyloxazoles via the reaction of a carboxylic acid halide with a 1,2-aminoalcohol and 2-alkoxypropene or 2,2-dialkoxypropane. The 2,2-dimethyloxazoles described herein are more commonly referred to in the art as acetonides and are referred to as acetonides herein. The acetonides are useful as intermediates in the preparation of HIV protease inhibitors.

References are made throughout this application to various published documents in order to more fully describe the state of the art to which this invention pertains. The disclosures of these references are hereby incorporated by reference in their entireties.

BACKGROUND OF THE INVENTION

U.S. Pat. No. 5,413,999 discloses N-substituted 2(R)-(substituted methyl)-4(S)-hydroxy-pentaneamide derivatives that are HIV protease inhibitors, including indinavir (referred to herein and in U.S. '999 as Compound J). The sulfate salt of indinavir is available from Merck under the tradename CRIXIVAN® for the treatment of HIV infection and AIDS. U.S. Pat. No. 5,646,148 discloses a class of N-substituted 2(R)-phenylmethyl-4(S)-hydroxy-pentaneamide derivatives which are potent HIV protease inhibitors, including N-(2(R)-hydroxy-1(S)-indanyl)-2(R)-phenylmethyl4(S)-hydroxy-5-(1 -(4-(2-benzo[b]furanylmethyl)-2(S)-N'-(t-butylcarboxamido)-piperazinyl))-pentaneamide (referred to herein as Compound K).

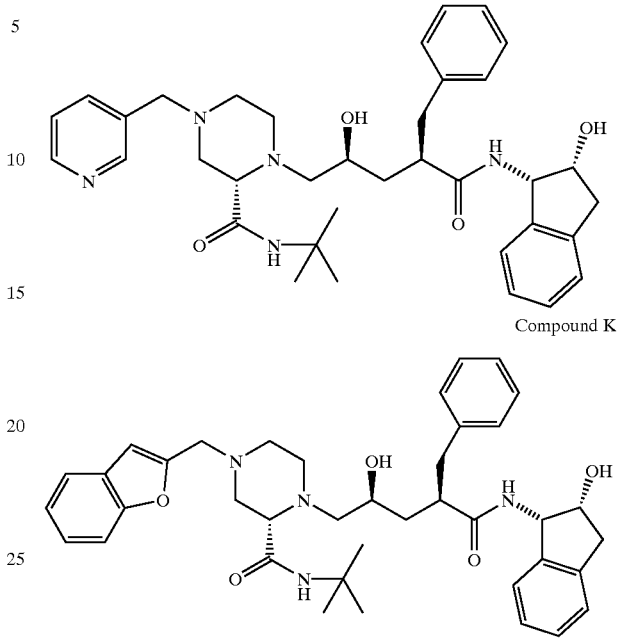

Compound J

Compound K

Acetonides are useful as intermediates for the preparation of 2(R)-phenylmethyl4(S)-hydroxy-pentaneamide derivatives, as exemplified by the following scheme for the preparation of the indinavir penultimate 10:

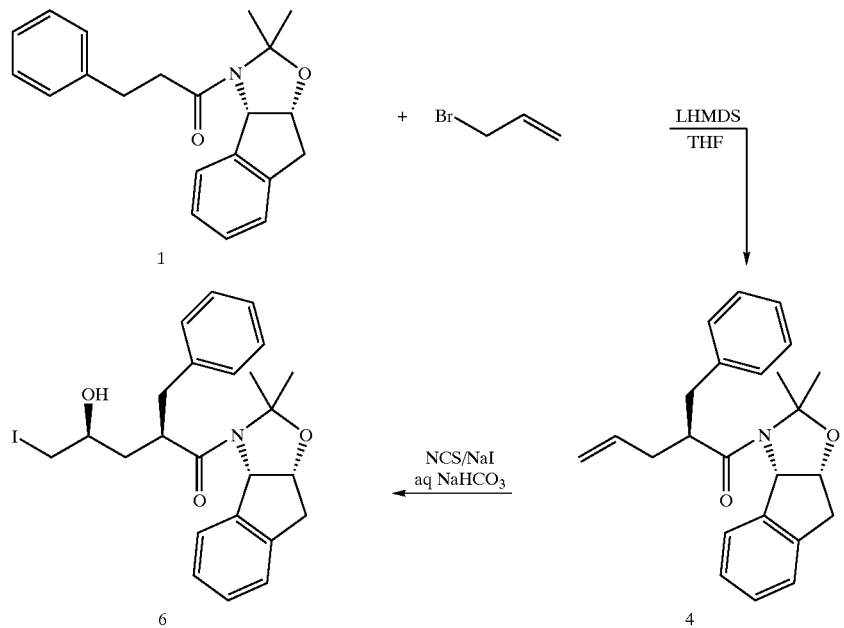

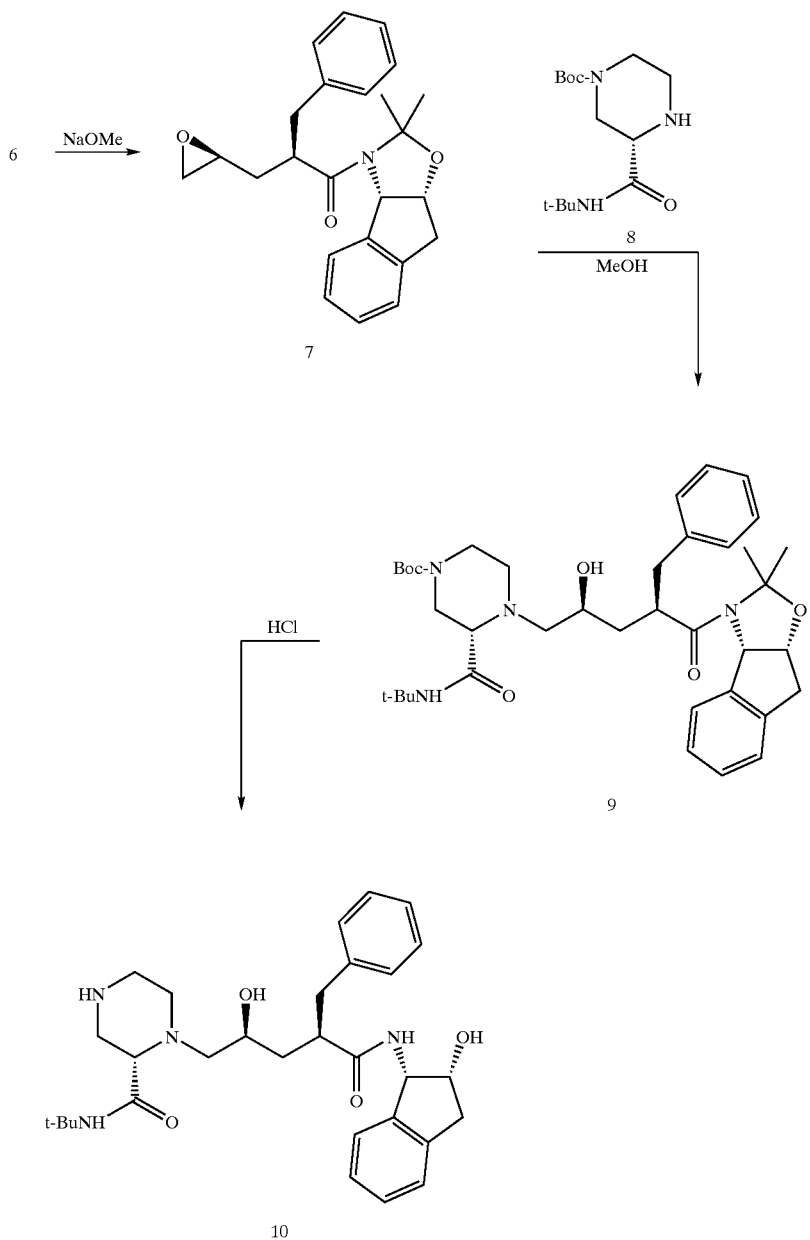

In the scheme, acetonide 1 is allylated with allyl bromide in the presence of LHMDS to obtain the allyl acetonide 4, which is converted to the iodohydrin 6 by treatment with NCS and an aqueous solution of NaI in the presence of sodium bicarbonate. Iodohydrin 6 is converted to epoxide 7 by treatment with sodium methoxide. (Alternatively, the acetonide 1 can be reacted with (S)-glycidyl tosylate in the presence of LHMDS to obtain epoxide 7 directly.) Epoxide 7 is then coupled with N-protected piperazine 8 in methanol to provide the alkylated Boc-piperazine 9. Treatment of 9 removes the Boc and acetonide protecting groups to afford the indinavir penultimate 10. Alkylation of 10 with 3-picolyl chloride provides Compound J (indinavir). A variety of other protease inhibiting compounds can be obtained by alkylating 10 with a suitable alkyl halide. Compound K, for example, can be obtained by alkylating 10 with 2-chloromethylbenzofuran. Further description of the preparation of N-substituted 2(R)-(substituted methyl)-4(S)-hydroxy-pentaneamide derivatives from acetonides can be found in U.S. Pat. No. 5,491,238, 5,728,840, WO 97/47632, and Askin, *Drug Discovery & Development* 1998, 1: 338–348.

Various methods for preparing acetonide 1 are known. The acetonide has been prepared in two steps by (1) treating hydrocinnamoyl chloride 2 with (−)-cis-1-aminoindan-2-ol 3 in a two-phase IPAc/aqueous potassium bicarbonate system at about 56–65° C. to give the corresponding hydrocinnamoyl amide 5, and then (2) drying 5 by distillation and reacting it in the same pot with 2-methoxypropene and methanesulfonic acid at about 40° C. to give the acetonide:

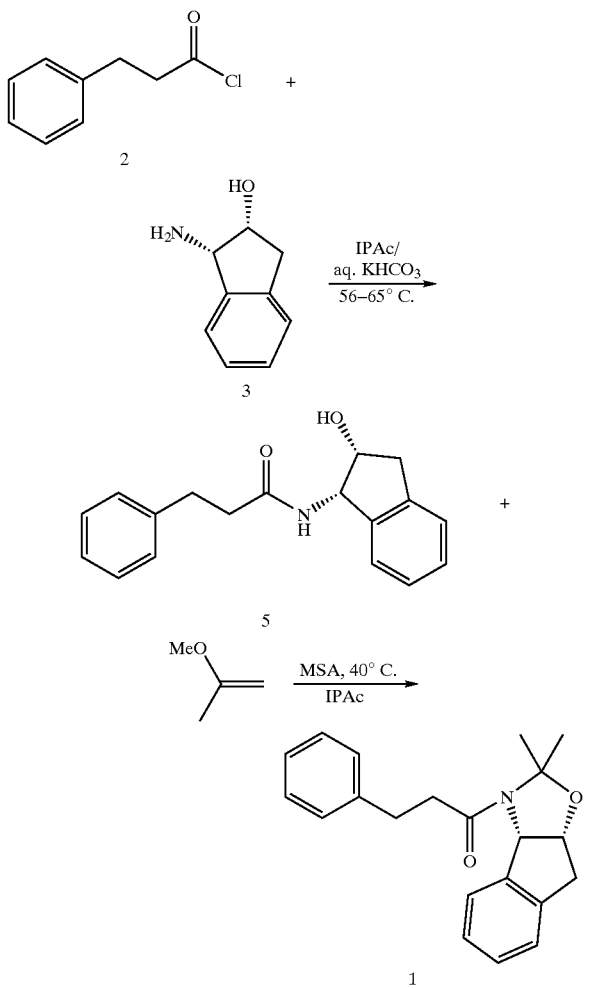

The acetonide-containing reaction product has then been distilled to remove by-product 2,2-dimethoxypropane and water, and solvent switched to THF for the allylation step.

Examples 24–26 of WO 97/47632 disclose two-step methods for preparing acetonide 1 which can be considered variations of the two-step method described in the preceding paragraph. A principal variation is the choice of solvent and reagent. The methods disclosed in Examples 24 and 25 employ diethoxymethane and sodium carbonate monohydrate instead of IPAc and aqueous potassium bicarbonate. In addition, Example 25 uses the tartrate salt methanol solvate of 3 instead of 3 per se. The method disclosed in Example 26 uses aqueous NaOH instead of aqueous potassium bicarbonate.

The above-described two-step methods have certain disadvantages. The reaction mixture in the first step consists of two phases—an aqueous phase and an organic phase. The phases must be separated at the conclusion of the reaction, and the organic phase containing the desired hydrocinnamoyl amide 5 must then be concentrated and dried (e.g., by atmospheric distillation) before it can be employed in the second step. Furthermore, the acetonide-containing mixture resulting from the second step cannot be used directly in the subsequent allylation. It must be solvent switched to a suitable solvent such as THF. Furthermore, the solvents employed in the two-step methods (i.e., IPAc and diethoxymethane) are relatively expensive compared to other organic solvents, and it would preferable to avoid their use in the large scale production of acetonide.

U.S. Pat. No. 5,491,238 (Example 1) discloses the preparation of acetonide 1 by reacting hydrocinnamoyl chloride 2 with (−)-cis-1-aminoindan-2-ol 3 at about 18–20° C. in THF and in the presence of triethylamine to provide hydroxyamide 3, and then treating the reaction mixture with pyridinium p-toluenesulfonate and then with 2-methoxypropene, and heating to 38–40° C. to afford 1. This method avoids the two-phase reaction system which characterizes the hydroxyamide formation step in the previously described methods, but it nonetheless has certain disadvantages. A by-product of hydroxyamide formation in the first step is the hydrochloride salt of $Et_3N$, which must be removed prior to the allylation step, because its presence would otherwise degrade or destroy the base (e.g., LHMDS) used in the allylation. The removal of the amine salt necessitates a number of additional processing steps, such as solvent switching from THF to IPAc or EtOAc after acetonide formation, washing the IPAc layer with water to remove $Et_3N.HCl$, and then isolating the acetonide by crystallization or solvent switching back to a solvent suitable for allylation (e.g., THF). Furthermore, the treatment of aqueous waste streams containing $Et_3N.HCl$ is costly, because direct disposal is precluded by environmental concerns. In addition to the problems posed by triethylamine, pyridinium p-toluenesulfonate is a very expensive reagent, and presents the same disposal problems as triethylamine.

U.S. Pat. No. 5,169,952 (Example 1) discloses reacting hydrocinnamic acid and cis-aminoindanol 3 in THF and in the presence of pivaloyl chloride and triethylamine at 25° C. to afford hydroxyamide 3, and then treating 3 slurried in methylene chloride with 2-methoxypropene and pyridinium p-toluenesulfonate at 25° C. to obtain acetonide 1. This preparative method is also disclosed in Askin et al., *J. Org. Chem.* 1992, 57: 2771–2773 (Supplemental Material). This method has the same disadvantages with respect to its use of triethylamine and pyridinium p-toluenesulfonate as the method of U.S. Pat. No. 5,491,238, as discussed in the preceding paragraph. An additional disadvantage is that methylene chloride is toxic and extremely expensive to use on a large scale due to environmental and reycling costs. Another disadvantage of the method is that it uses pivaloyl chloride to generate hydrocinamoyl chloride from the hydrocinnamic acid in situ. This results in the formation of pivalic acid as an additional by-product, which must also be removed from the acetonide product and disposed of.

Reaction of acetonide 1 in THF with allylating agents (particularly allyl bromide) in the presence of LHMDS to obtain allyl acetonide 4 has been disclosed in U.S. Pat. No. 5,728,840, WO 97/47632, and Askin, *Drug Discovery & Development* 1998, 1: 338–348.

SUMMARY OF THE INVENTION

The present invention is directed to improved processes for preparing acetonides. The present invention includes a process for preparing an acetonide of Formula (I):

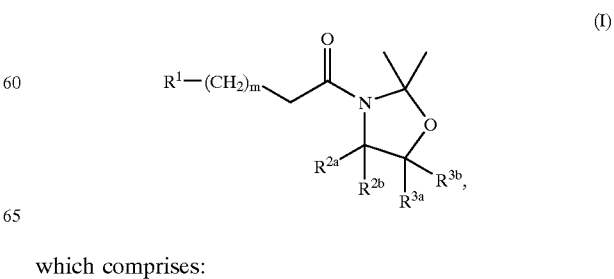

which comprises:

(A) reacting an acid halide of Formula (II):

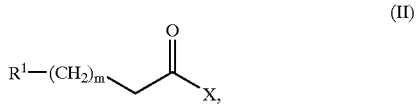
(II)

with an alkoxy compound which is 2-alkoxypropene or 2,2-dialkoxypropane and an aminoalcohol of Formula (III):

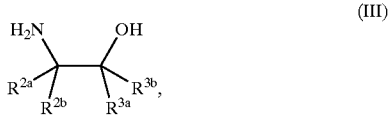
(III)

in the presence of inorganic base and an ether as solvent, the reaction mixture having a single liquid phase, to form Compound I;
wherein
$R^1$ is
 (1) hydrogen;
 (2) $C_1$–$C_6$ alkyl;
 (3) $C_1$–$C_6$ alkyl substituted with one or more substituents, each of which is independently hydroxy, cyano, or halo;
 (4) $C_3$–$C_9$ cycloalkyl;
 (5) $C_3$–$C_8$ cycloalkyl substituted with one or more substituents, each of which is independently $C_1$–$C_4$ alkyl, hydroxy, cyano, or halo;
 (6) aryl;
 (7) aryl substituted with one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^aCO$—$NR^aR^b$, —$S(O)_k$—$R^a$ wherein k is an integer from 0 to 2, —$S(O)_2$—$NR^aR^b$, —$NR^aS(O)_2$—$R^b$, or —$NR^aS(O)_2$—$NR^aR^b$;
 (8) heterocycle; or
 (9) heterocycle substituted one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^aCO$—$NR^aR^b$, —$S(O)_k$—$R^a$ wherein k is an integer from 0 to 2, —$S(O)_2$—$NR^aR^b$, —$NR^aS(O)_2$—$R^b$, or —$NR^aS(O)_2$—$NR^aR^b$;
$R^{2a}$, $R^{2b}$, $R^{3a}$ and $R^{3b}$ each independently have the same definition as $R^1$; or
$R^{2a}$ and $R^{3a}$ each independently have the same definition as $R^1$, and $R^{2b}$ and $R^{3b}$ together with the carbon atoms to which each is attached form
 (1) a carbocycle;
 (2) a carbocycle substituted with one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^aCO$—$NR^aR^b$, —$S(O)_k$—$R^a$ wherein k is an integer from 0 to 2, —$S(O)_2$—$NR^aR^b$, —$NR^aS(O)_2$—$R^b$, or —$NR^aS(O)_2$—$NR^aR^b$;
 (3) a heterocycle; or
 (4) a heterocycle substituted with one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^aCO$—$NR^aR^b$, —$S(O)_k$—$R^a$ wherein k is an integer from 0 to 2, —$S(O)_2$—$NR^aR^b$, —$NR^aS(O)_2$—$R^b$, or —$NR^aS(O)_2$—$NR^aR^b$;

each $R^a$ and $R^b$ is independently hydrogen or $C_1$–$C_4$ alkyl;
X is halogen; and
m is an integer from 0 to 5.

An embodiment of the above-described process of the present invention is a process for preparing an acetonide of Formula (I'):

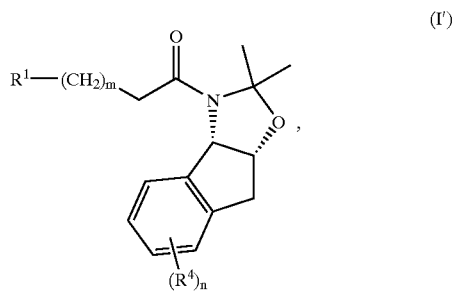
(I')

which comprises:
 (A) reacting an acid halide of Formula (II):

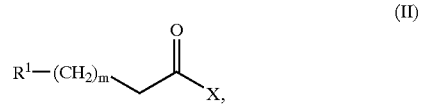
(II)

with an alkoxy compound which is 2-alkoxypropene or 2,2-dialkoxypropane and a cis-aminoindanol of Formula (III'):

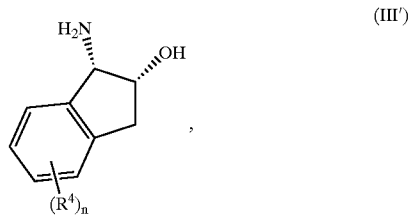
(III')

in the presence of inorganic base and an ether as solvent, the reaction mixture having a single liquid phase, to form Compound I';
wherein
$R^1$ and m are as heretofore defined;
each $R^4$ is independently
 (1) $C_1$–$C_4$ alkyl;
 (2) halogenated $C_1$–$C_4$ alkyl;
 (3) $C_1$–$C_4$ alkoxy,
 (4) halogenated $C_1$–$C_4$ alkoxy
 (5) hydroxy,
 (6) cyano,
 (7) halo,
 (8) —$CO_2R^c$,
 (9) —$COR^c$,

(10) —NR$^c$R$^d$,
(11) —NR$^c$—COR$^d$,
(12) —NR$^c$—CO$_2$R$^d$,
(13) —CO—NR$^c$R$^d$,
(14) —OCO—NR$^c$R$^d$,
(15) —NR$^c$CO—NR$^c$R$^d$,
(16) —S(O)$_k$—R$^c$ wherein k is an integer from 0 to 2,
(17) —S(O)$_2$—NR$^c$R$^d$,
(18) —NR$^c$S(O)$_2$—R$^d$, or
(19) —NR$^c$S(O)$_2$—NR$^c$R$^d$;

each R$^c$ and R$^d$ is independently hydrogen or C$_1$–C$_4$ alkyl; and n is an integer from 0 to 4.

The present invention also includes a process which, in addition to Step A as defined and described above, comprises:

(B) reacting the acetonide of Formula (I) with an allylation agent in strong base and in an ether solvent to form an allyl acetonide of Formula (IV):

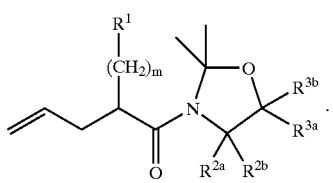

(IV)

In an embodiment of this process, Step A involves the preparation of an acetonide of Formula (I') as described above, and Step B comprises reacting the acetonide of Formula (I') with an allylation agent in strong base and in an ether solvent to form an allyl acetonide of Formula (IV'):

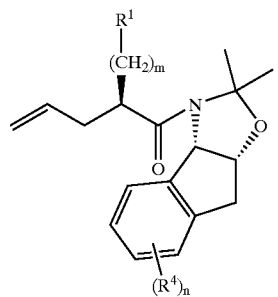

(IV')

A preferred aspect of the allylation step is the use of an allyl halide (e.g., allyl bromide) as the allylation agent.

The above-described process of the present invention represents an improvement over known methods for producing acetonides, because the inventive process forms the desired acetonide in a single step; i.e., it avoids the isolation and/or separate work-up of an hydroxyamide intermediate, and it avoids the use of MSA. Furthermore, the reaction system has a single liquid phase, and is typically also anhydrous, and thereby avoids the additional processing steps associated with a two-phase system, such as separation and treatment of the phases at the conclusion of the reaction. The process can also employ ether solvents such as THF which can be less expensive than the solvents used in known methods (e.g., IPAc). In addition, because the process is conducted in an ether solvent such as THF, the reaction batch can be used directly in allylation Step B; i.e., solvent switching is avoided.

The present invention also includes an improved two-step process for making acetonides. More particularly, the present invention includes a process for preparing an acetonide of Formula (I) which comprises (C) reacting an acid halide of Formula (II):

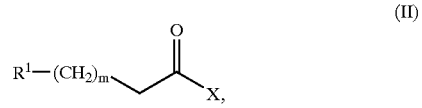

(II)

with an aminoalcohol of Formula (III):

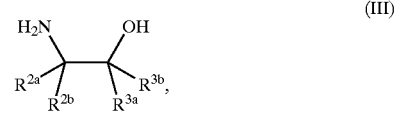

(III)

in the presence of LiOH and an ether as solvent, the reaction mixture having a single liquid phase, to form a compound of Formula (V):

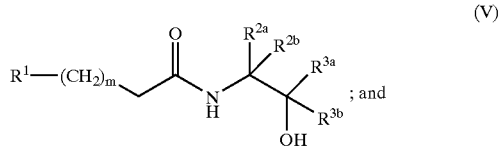

(V)

(D) reacting Compound V from Step C with an alkoxy compound which is 2-alkoxypropene or 2,2-dialkoxypropane in the presence of acid and ether solvent to form acetonide I;

wherein R$^1$, R$^{2a}$, R$^{2b}$, R$^{3a}$, R$^{3b}$, X, and m are as defined above.

An embodiment of this process is a process for preparing an acetonide of Formula (I') which comprises:

(C) reacting an acid halide of Formula (II) with a cis-aminoindanol of Formula (III') in the presence of LiOH and an ether as solvent, the reaction mixture having a single liquid phase, to form a compound of Formula (V'):

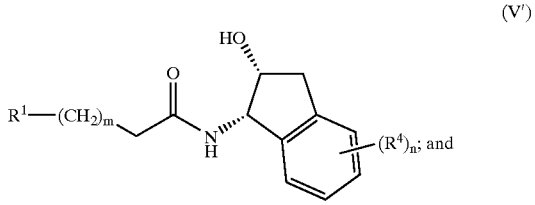

(V')

(D) reacting Compound V' from Step C with an alkoxy compound which is 2-alkoxypropene or 2,2-dialkoxypropane in the presence of acid and ether solvent to form acetonide I';

wherein R$^1$, R$^4$, m and n are as defined above.

The present invention also includes a process which, in addition to Steps C and D as defined and described above, comprises:

(E) reacting the acetonide of Formula (I) with an allylation agent in strong base and in an ether solvent to form an allyl acetonide of Formula (IV).

In an embodiment of this process, Steps C and D involve the preparation of an acetonide of Formula (I') as described above, and Step E comprises reacting the acetonide of Formula (I') with an allylation agent (e.g., an allyl halide such as allyl bromide) in strong base and in an ether solvent to form an allyl acetonide of Formula (IV').

The two-step process of the present invention and embodiments thereof represent an improvement over known two-step methods for producing acetonides. The reaction mixture of Step C has a single liquid phase, which avoids the additional processing steps associated with known methods involving aqueous/organic two-phase systems, such as separation and treatment of the phases at the conclusion of the reaction. The by-products from LiOH neutralization in Step C are water and Li halide. The water can be readily removed during or after Step C (e.g., by distillation) thereby maintaining the single phase. In contrast to the known two-step method employing anhydrous $Et_3N$ as the base and producing $Et_3N \cdot HCl$ by-product, the Li halide need not be removed from the acetonide product before commencing the allylation step. In fact, the presence of Li halide (e.g., LiCl) in the Step E reaction mixture has unexpectedly been found to enhance the stereoselectivity of the allylation. Furthermore, because LiCl is also relatively non-toxic, it can be disposed of directly. Still another advantage of the two-step method of the invention is that the reaction batch from Step D, which employs an ether solvent such as THF, can be used directly in the allylation step thus avoiding a solvent switch.

Other embodiments, aspects and features of the present invention are either further described in or will be apparent from the ensuing description, examples and appended claims.

DETAILED DESCRIPTION OF THE INVENTION

The present invention is directed to improved processes for preparing acetonides. The present invention includes a single step process for forming acetonides by reacting a carboxylic acid halide with a 1,2-aminoalcohol and an alkoxy compound which is 2-alkoxypropene or 2,2-dialkoxypropane in an ether solvent and in the presence of an inorganic base. This process is set forth above in the Summary of the Invention as Step A.

In this process, the $R^1$ group in the definition of acid halide II is (1) hydrogen; (2) $C_1-C_6$ alkyl; (3) $C_1-C_6$ alkyl substituted with one or more substituents, each of which is independently hydroxy, cyano, or halo; (4) $C_3-C_8$ cycloalkyl; (5) $C_3-C_8$ cycloalkyl substituted with one or more substituents, each of which is independently $C_1-C_4$ alkyl, hydroxy, cyano, or halo; (6) aryl; (7) aryl substituted with one or more substituents, each of which is independently $C_1-C_4$ alkyl, halogenated $C_1-C_4$ alkyl, $C_1-C_4$ alkoxy, halogenated $C_1-C_4$ alkoxy, hydroxy, cyano, halo, phenyl, $-CO_2R^a$, $-COR^a$, $-NR^aR^b$, $-NR^a-COR^b$, $-NR^b-CO_2R^b$, $-CO-NR^aR^b$, $-OCO-NR^aR^b$, $-NR^aCO-NR^aR^b$, $-S(O)_k-R^a$ wherein k is an integer from 0 to 2, $-S(O)_2-NR^aR^b$, $-NR^aS(O)_2-R^b$, or $-NR^aS(O)_2-NR^aR^b$; (8) heterocycle; or (9) heterocycle substituted one or more substituents, each of which is independently $C_1-C_4$ alkyl, halogenated $C_1-C_4$ alkyl, $C_1-C_4$ alkoxy, halogenated $C_1-C_4$ alkoxy, hydroxy, cyano, halo, phenyl, $-CO_2R^a$, $-COR^a$, $-NR^aR^b$, $-NR^aCOR^b$, $-NR^b-CO_2R^b$, $-CO-NR^aR^b$, $-OCO-NR^aR^b$, $-NR^aCO-NR^aR^b$, $-S(O)_k-R^a$ wherein k is an integer from 0 to 2, $-S(O)_2-NR^aR^b$, $-NR^aS(O)_2-R^b$, or $-NR^aS(O)_2-NR^aR^b$.

In one embodiment, $R^1$ is aryl, substituted aryl, heterocycle, or substituted heterocycle. In another embodiment, $R^1$ is aryl or substituted aryl (e.g., phenyl or substituted phenyl). In an aspect of this embodiment, $R^1$ is phenyl. In another embodiment, $R^1$ is phenyl, substituted phenyl, heterocycle or substituted heterocycle, wherein heterocycle is selected from the group consisting of pyrrolidinyl, pyrazolyl, pyridyl, pyrazinyl, pyrimidinyl, and pyridazinyl. In still another embodiment, $R^1$ is phenyl, substituted phenyl, pyridyl, or substituted pyridyl.

In one embodiment, when $R^1$ is substituted aryl (or is substituted heterocycle), each of the one or more substituents is independently $C_1-C_4$ alkyl, halogenated $C_1-C_4$ alkyl, $C_1-C_4$ alkoxy, halogenated $C_1-C_4$ alkoxy, hydroxy, cyano, halo, phenyl, $-CO_2R^a$, or $-COR^a$. In another embodiment, each of the substituents on substituted aryl (or substituted heterocycle) is independently $C_1-C_4$ alkyl, fluorinated $C_1-C_4$ alkyl, $C_1-C_4$ alkoxy, fluorinated $C_1-C_4$ alkoxy, hydroxy, cyano, or fluoro. In still another embodiment, each of the substituents is independently $C_1-C_4$ alkyl, $(CH2)_{0-3}CF_3$, $C_1-C_4$ alkoxy, or $O(CH_2)_{0-3}CF_3$, cyano, or fluoro. In yet another embodiment, each of the substituents is independently methyl, ethyl, $CF_3$, $OCF_3$, cyano, or fluoro.

Certain of the substituent definitions set forth herein include groups $R^a$ and/or $R^b$. Each of $R^a$ and $R^b$ is independently hydrogen or $C_1-C_4$ alkyl. In one embodiment, each of $R^a$ and $R^b$ is independently hydrogen or $C_1-C_4$ alkyl; provided that when $R^a$ is attached to N, $R^a$ is not hydrogen; and further provided when $R^b$ is attached to N, $R^b$ is not hydrogen. In another embodiment, each of $R^a$ and $R^b$ is independently hydrogen, methyl, or ethyl. In still another embodiment, each of $R^a$ and $R^b$ is independently methyl or ethyl.

The integer m defines the number of methylene groups bridging $R^1$ to the acetyl halide functional group in Compound II, and has a value in the range of from 0 to 5. In other embodiments, m is 0 to 4, or is 0 to 3; or is 1 to 3; or is 0 to 2; or is 1 to 2; or is 0 to 1; or is 1; or is 0. In an aspect of the process of the invention, the process comprises Step A as set forth above wherein m is one; i.e., the acid halide II reactant is $R^1-CH_2CH_2C(=O)X$. In a further aspect of the invention, the process comprises Step A as set forth above, wherein $R^1$ is aryl or substituted aryl, and m is an integer from 0 to 2.

X in Compound II is halogen. In one embodiment, X is chloro or bromo. In an aspect of this embodiment, X is chloro.

Exemplary acid halides suitable for use in Step A of the process of the invention include alkanoyl halides of formula $R^*-C(=O)X$, wherein $R^*$ is $C_1-C_6$ alkyl (e.g., acetyl chloride, acetyl bromide, propionyl chloride, butyryl chloride, isobutyryl chloride, valeryl chloride, and caproyl chloride) and phenylalkanoyl halides of formula $Ph(CH_2)_{1-6}C(=O)X$ (e.g., phenylacetyl chloride, hydrocinnamyl chloride (which may also be referred to as 3-phenylpropionyl chloride), 4-phenylbutyryl chloride, and 3-pyridylpropionyl chloride).

$R^{2a}$, $R^{2b}$, $R^{3a}$ and $R^{3b}$ in the definition of aminoalcohol $R^1$ each independently have the same definition as $R^1$, and have embodiments analogous to the embodiments of $R^1$ as set forth above. In another embodiment, $R^{2a}$ and $R^{3a}$ are both hydrogen, and $R^{2b}$ and $R^{3b}$ each independently have the same definition as $R^1$ or the same definition as one of the embodiments of $R^1$ as set forth above.

Alternatively, $R^{2a}$ and $R^{3a}$ each independently have the same definition as $R^1$ (or an embodiment thereof), and $R^{2b}$ and $R^{3b}$ together with the carbon atoms to which each is attached form (1) a carbocycle; (2) a carbocycle substituted with one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^a$CO—$NR^aR^b$, —$S(O)_k$—$R^a$ wherein k is an integer from 0 to 2, —$S(O)_2$—$NR^aR^b$, —$NR^aS(O)_2$—$R^b$, or —$NR^aS(O)_2$—$NR^aR^b$; (3) a heterocycle; or (4) a heterocycle substituted with one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, —$COR^a$, —$NR^aR^b$, $NR^a$—$COR^b$, —$NR^b$—$CO_2R^b$, —CO—$NR^aR^b$, —OCO—$NR^aR^b$, —$NR^a$CO—$NR^aR^b$, —$S(O)_k$—$R^a$ wherein k is an integer from 0 to 2, —$S(O)_2$—$NR^aR^b$, —$NR^aS(O)_2$—$R^b$, or —$NR^aS(O)_2$—$NR^aR^b$.

In one embodiment, $R^{2b}$ and $R^{3b}$ together with the carbon atoms to which each is attached form a carbocycle or a substituted carbocycle. In an aspect of the foregoing embodiment, the carbocycle is cyclopentyl, cyclohexyl, cycloheptyl, indanyl, tetralinyl, or decalinyl. In another aspect of this embodiment, $R^{2a}$ and $R^{3a}$ are both hydrogen.

In one embodiment, when $R^{2b}$ and $R^{3b}$ together with the carbon atoms to which each is attached form a substituted carbocycle (or substituted heterocycle), each of the one or more substituents is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, or —$COR^a$. In another embodiment, each of the substituents on substituted carbocycle (or substituted heterocycle) is independently $C_1$–$C_4$ alkyl, fluorinated $C_1$–$C_4$ alkyl, $C_1$–$C_4$ alkoxy, fluorinated $C_1$–$C_4$ alkoxy, hydroxy, cyano, or fluoro. In still another embodiment, each of the substituents is independently $C_1$–$C_4$ alkyl, $(CH_2)_{0-3}CF_3$, $C_1$–$C_4$ alkoxy, or $O(CH_2)_{0-3}CF_3$, cyano, or fluoro. In yet another embodiment, each of the substituents is independently methyl, ethyl, $CF_3$, $OCF_3$, cyano, or fluoro.

Exemplary 1,2-aminoalcohols suitable for use in Step A of the process of the invention include the vicinal aminoalcohols of cyclopentane, cyclohexane, cycloheptane, indane, tetralin, decalin, benzosuberane, chroman (e.g., 4-aminochroman-3-ol), isochroman, thiochroman, and tetrahydroquinoline; the vicinal aminoalcohols of $C_2$–$C_{14}$ alkanes (e.g., ethanolamine, 1-amino-2-hydroxy-propane, 1-amino-2-hydroxybutane, and 2-amino-3-hydroxybutane); and vicinal aminoalcohols of phenyl substituted $C_2$–$C_8$ alkanes (e.g., norephredine). It is understood that the foregoing list of exemplary 1,2-aminoalcohols includes the optical isomers of those aminoalcohols containing one or more chiral carbon atoms (e.g., (1R,2S)-norephedrine, (1S)-amino-(2R)-indanol, and R,R- and S,S4-aminochroman-3-ol) and mixtures thereof.

In a preferred embodiment, the 1,2-aminoalcohol is a cis-aminoindanol of Formula (III'):

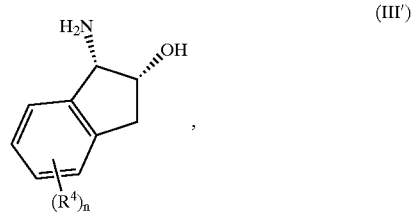

(III')

which provides upon reaction in Step A with an alkoxy compound which is 2-alkoxypropene or 2,2-dialkoxypropane and an acid halide II as heretofore defined, an acetonide of Formula (I'):

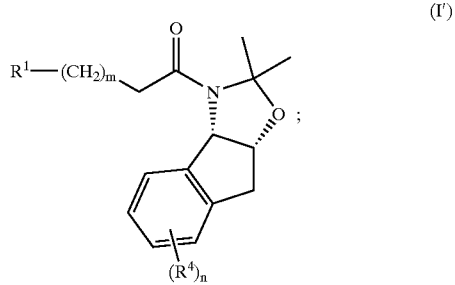

(I')

wherein each $R^4$ is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, —$CO_2R^c$, —$COR^c$, —$NR^cR^d$, —$NR^c$—$COR^d$, —$NR^c$—$CO_2R^d$, —CO—$NR^cR^d$, —OCO—$NR^cR^d$, —$NR^cCO$—$NR^cR^d$, —$S(O)_k$—$R^c$ wherein k is an integer from 0 to 2, —$S(O)_2$—$NR^cR^d$, —$NR^cS(O)_2$—$R^d$, or —$NR^cS(O)_2$—$NR^cR^d$;

each $R^c$ and $R^d$ is independently hydrogen or $C_1$–$C_4$ alkyl; and n is an integer from 0 to 4.

Aspects of the process described in the preceding embodiment include use of a cis-aminoalcohol of Formula (III') wherein:

(a) each $R^4$ is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^c$, or —$COR^c$;

(b) each $R^4$ is independently $C_1$–$C_4$ alkyl, fluorinated $C_1$–$C_4$ alkyl, $C_1$–$C_4$ alkoxy, fluorinated $C_1$–$C_4$ alkoxy, hydroxy, cyano, or fluoro;

(c) each $R^4$ is independently $C_1$–$C_4$ alkyl, $(CH_2)_{0-3}CF_3$, $C_1$–$C_4$ alkoxy, or $O(CH_2)_{0-3}CF_3$, cyano, or fluoro;

(d) each $R^4$ is independently methyl, ethyl, $CF_3$, $OCF_3$, cyano, or fluoro;

(e) each of $R^c$ and $R^d$ is independently hydrogen or $C_1$–$C_4$ alkyl; provided that when $R^c$ is attached to N, $R^c$ is not hydrogen; and further provided when $R^d$ is attached to N, $R^d$ is not hydrogen;

(f) each of $R^c$ and $R^d$ is independently hydrogen, methyl, or ethyl;

(g) each of $R^c$ and $R^d$ is independently methyl or ethyl; and (h) each $R^4$ is as defined in (a), and $R^c$ is as defined in any one of (e) to (g).

The alkoxy compound employed as a reactant in Step A can be either a 2-alkoxypropene or a 2,2-dialkoxypropane. The 2-alkoxypropene is typically any of the 2-($C_1$–$C_6$ alkoxy)propenes, such as 2-methoxypropene, 2-ethoxypropene, 2-n-propoxypropene, or 2-isopropoxypropene. The 2,2-dialkoxy propane is typically any of the 2,2-(di-$C_1$–$C_6$ alkoxy)propanes, such as 2,2-dimethoxypropane, 2,2-diethoxypropane, or 2-ethoxy-2-methoxypropane. In one embodiment, the alkoxy compound is a 2-alkoxypropene. In an aspect of this embodiment, the 2-alkoxypropene is 2-methoxypropene.

The inorganic base in Step A can be any inorganic base which can scavenge the hydrohalide by-product resulting from the amidation of aminoalcohol III by acid halide II, so as to maintain neutral reaction conditions and prevent degradation of the acetonide I product by hydrolysis. The inorganic base can be a basic salt of an alkali metal or an alkaline earth metal. In one embodiment, the inorganic base is selected from the group consisting of alkali metal hydroxides, oxides, carbonates, and bicarbonates. Exemplary bases include LiOH, NaOH, KOH, LiHCO$_3$, NaHCO$_3$, KHCO$_3$, Na$_2$O, K$_2$O, Li$_2$CO$_3$, Na$_2$CO$_3$, and K$_2$CO$_3$. The inorganic base can be in the form of a hydrate or it can be anhydrous (e.g., anhydrous LiOH), and is typically anhydrous.

The alkali metal hydroxides and carbonates, especially LiOH and NaHCO$_3$, are particularly suitable for use in Step A, being capable of providing acetonide I in high yield and purity. While not wishing to be bound by any particular theory, it is believed that these bases can have limited solubility and/or reactivity in the Step A reaction medium which permits a hydrohalic acid lifetime that is sufficiently long to enable acid catalysis of acetonide formation, but is not so long as to result in an acid buildup that would cause undesirable side reactions. The use of LiOH in this process is particularly advantageous since the byproduct Li halide (e.g., LiCl) is soluble in most ether solvents (e.g. THF) under the given conditions, ultimately providing thereby a homogeneous product mixture, which significantly simplifies the subsequent transfer/work-up/cool-down steps. In addition, as detailed below, the presence of Li halide enhances the stereoselectivity of the subsequent allylation step.

The solvent in Step A is an ether solvent. Suitable ethers include dialkyl ethers wherein each alkyl is independently a C$_1$–C$_6$ alkyl, C$_4$–C$_6$ cyclic ethers and diethers, ethylene glycol ethers, and C$_6$–C$_8$ aromatic ethers. Exemplary ether solvents include ethyl ether, n-butyl ether, methyl tert-butyl ether, THF, dioxane, diglyme (i.e., diethylene glycol dimethyl ether), anisole, and phenetole. In one embodiment, the ether is THF.

The reaction of Step A can be conducted over a wide temperature range. The temperature is suitably in the range of from about 0 to about 80° C. (e.g., from about 15 to about 80° C.), and is typically in the range of from about 20 to about 60° C.

The maximum conversion of Compound III and maximum yield of Compound I is normally desired, and relative proportions of reactants and reagents suitable for this purpose are typically employed. On the other hand, the scope of Step A includes any and all proportions of reactants and reagents which will result in the formation of at least some of Compound I.

Acyl halide II is typically employed in an amount of at least about one equivalent per equivalent of aminoalcohol III. In one embodiment, the acid halide is employed in an amount in the range of from about 1 to about 2 equivalents per equivalent of Compound III. In another embodiment, the amount of acid halide is in the range of from about 1 to about 1.2 equivalents per equivalent of III.

The alkoxy compound (e.g., a 2-alkoxypropene such as 2-methoxypropene) is typically employed in an amount of at least about 1.8 equivalents per equivalent of aminoalcohol III. In one embodiment, the alkoxy compound (e.g., 2-methoxypropene) is employed in an amount in the range of from about 3.8 to about 10 equivalents per equivalent of Compound III. In another embodiment, the amount of the alkoxy compound is in the range of from about 3.8 to about 5.5 equivalents per equivalent of III.

The inorganic base is typically employed in an amount of at least about 0.5 equivalents per equivalent of aminoalcohol III. In one embodiment, the inorganic base is employed in an amount in the range of from about 0.5 to about 2 equivalents per equivalent of Compound III. In another embodiment, the amount of inorganic base is in the range of from about 0.5 to about 1 equivalent per equivalent of III.

The base must be charged to the reaction vessel (or reaction "pot") before the acid halide II, but otherwise the order of addition of the reactants and reagents is not critical. In one embodiment, the inorganic base, ether solvent, and aminoalcohol III are charged to the reaction vessel to form a slurry, followed by addition of the alkoxy compound (e.g., 2-alkoxypropene) and then the slow addition of acid halide II. Addition of Compound II is exothermic, so that suitable temperature control is required. Dry reagents and reactants are employed, and the reaction mixture is generally free of moisture at the start of the reaction. The slurry is typically agitated (e.g., stirred) during addition of the reactants and reagents, and the reaction mixture is typically agitated during the subsequent reaction.

The reaction mixture in Step A can be characterized as having a single liquid phase under the Step A reaction conditions. The single liquid phase is a predominantly organic phase, which, apart from certain of the bases suitable for use in Step A, contains all of the reaction components (i.e., reactants, reagents, product, and by-products) in solution. Certain bases (e.g., NaHCO$_3$) and by-products therefrom (e.g., NaCl) can be incompletely dissolved in the liquid phase during the reaction. However, some of the bases (e.g., LiOH) and their by-products (LiCl) are typically completely dissolved in the liquid phase, providing thereby a homogeneous reaction mixture having all of the reaction components present only in the single liquid phase.

The reaction mixture in Step A is typically also anhydrous, which means that the reaction mixture contains little or no moisture. The reaction mixture at the start of the reaction suitably has a KF value equal to or less than about 2000 mg/liter. In one embodiment, the KF of the reaction mixture at the start of the reaction is equal to or less than about 1100 mg/L. The reaction mixture will remain relatively dry during the reaction because the alkoxy compound will react with by-product water formed during the reaction; e.g., 2-methoxypropene will react with water to afford methanol and acetone.

The progress of the reaction in Step A can be followed by monitoring the disappearance of Compounds II or III and/or the appearance of Compound I using, for example, TLC, HPLC, NMR or GC.

Compound I can be recovered from the Step A reaction mixture at the conclusion of the reaction by conventional means; e.g., quenching excess acid in the reaction mixture by addition of more base, filtering, switching to a less polar solvent such as IPAc or cyclohexane, washing with water, concentrating by evaporative or vacuum removal of a portion of the solvent, crystallizing I. from the concentrate, separating crystallized I by filtration, and washing and drying the filter cake. When Compound I is to be allylated (Step B, described below), it is typically not recovered from the reaction mixture. Instead the Step A reaction mixture is typically employed directly in the allylation, after suitable work-up (e.g., distillative removal of residual moisture and 2,2-dialkoxypropane by-product, followed by dilution with additional ether solvent). Step A reaction mixtures resulting from the use of LiOH as base can be particularly advantageous for direct use in allylation Step B, because such mixtures contain Li halide (e.g., LiCl via neutralization of HCl). The presence of Li halide in the mixtures has unexpectedly been found to enhance the stereoselectivity of the allyl product of Step B.

The present invention also includes a process which comprises Step A described above and allylation Step B, which is (B) reacting the acetonide of Formula (I) with an allylation agent in is strong base and in an ether solvent to form an allyl acetonide of Formula (IV):

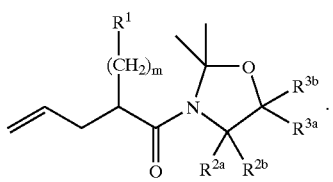

wherein $R^1$, $R^{2a}$, $R^{2b}$, $R^{3a}$, $R^{3b}$, and m are as heretofore defined.

In a preferred embodiment, allylation Step B affords an allyl acetonide of Formula (IV'):

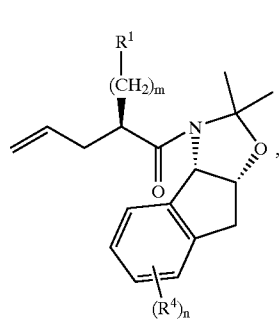

by reaction of an acetonide of Formula (I'), prepared in accordance with Step A as already described, with an allylation agent in strong base and in an ether solvent.

The allylation agent can be an allyl halide (e.g., allyl chloride, allyl bromide or allyl iodide), or it can be an allyl electrophile (e.g., allyl methane sulfonate or allyl esters) in the presence of a transition metal catalyst. The allylation agent is preferably an allyl halide, and is typically allyl bromide.

As used in this context, "strong base" means any base which is capable of deprotonating the acetonide under the reaction conditions employed for the allylation. Strong bases suitable for use in Step B include alkali metal salts and alkaline earth metal salts of di-$C_1$–$C_6$ alkylamines and $C_4$–$C_8$ cyclic secondary amines, alkali metal salts and alkaline earth metal salts of bis(tri-$C_1$–$C_4$ alkylsilyl)amines, alkali metal amides, $C_1$–$C_6$ alkyllithiums, $C_6$–$C_{10}$ aryllithiums, $C_1$–$C_6$ alkylmagnesium halides, and $C_1$–$C_6$ alkoxides of alkali and alkaline earth metals. Exemplary bases include the lithium, sodium, potassium or magnesium salts of diethylamine, disopropylamine, dicyclohexylamine, piperidine, pyrrolidine, or bistrimethylsilylamine; n-, iso-, sec-, and tert-butyllithium, methyllithium, ethyllithium, and phenyllithium; methyl ethyl, propyl, or butyl magnesium halide; the methoxides, ethoxides, isopropoxides, tert-butoxides, tert-amyloxides of lithium, sodium, potassium, or magnesium. A preferred base is lithium hexamethyldisilazide ("LHMDS").

Suitable ether solvents are the same as those described above for use in Step A.

The temperature range for the allylation is suitably from about −78 to about 30° C, and is typically from about 40 to about −25° C. The incubation period is typically at least about 15 minutes (e.g., up to about 5 hours).

The maximum conversion of Compound I and maximum yield of Compound IV is normally desired, and relative proportions of reactants and reagents suitable for this purpose are typically employed. The allylation agent (e.g., allyl halide) is suitably employed in an amount of at least about 1 equivalent per equivalent of acetonide I. In one embodiment, the allylation agent is employed in an amount in the range of from about 1 to about 5 equivalents per equivalent of Compound I. In another embodiment, the amount of allylation agent is in the range of from about 1 to about 1.2 equivalents per equivalent of Compound I.

The strong base is suitably employed in an amount of at least about 1 equivalent per equivalent of acetonide I. In one embodiment, the base is employed in an amount in the range of from about 1 to about 5 equivalents per equivalent of Compound I. In another embodiment, the amount of base is in the range of from about 1 to about 1.1 equivalents per equivalent of Compound I.

The order of addition of the reactants and reagents to the reaction vessel (or reaction "pot") in Step B is not critical. The reactants and reagents can, for example, be added concurrently, either together or separately, or they can be added sequentially in any order. In one embodiment, the allylation agent (e.g., allyl halide) is added to an ether solvent-acetonide I mixture, followed by addition of the strong base in ether solvent. As already noted above, the acetonide I is typically not isolated from the Step A reaction mixture. Instead the mixture is used directly in Step B, wherein the allylation agent and strong base are added directly thereto.

The progress of the reaction in Step B can be followed by monitoring the disappearance of Compound I and/or the appearance of Compound IV using, for example, TLC, HPLC, NMR or GC.

Allyl acetonide IV can be recovered from the reaction mixture at the completion of the reaction by conventional means; e.g., quenching excess base in the reaction by addition of acid (e.g., citric acid), concentrating the reaction mixture by evaporative or vacuum removal of solvent, switching solvent to a less polar solvent (e.g., IPAc or cyclohexane), and then cooling to precipitate and isolate the allyl acetonide product. The allyl acetonide need not be isolated, but can instead be left in solution for further reaction. Allyl acetonide 4, for example, is typically solvent switched from an ether solvent to an acetate solvent (e.g., from THF to IPAc) for conversion to the corresponding iodohydrin, from which Compound J, Compound K and related compounds can ultimately be prepared (see, e.g., Askin, *Drug Discovery & Development* 1998, 1: 338–348 and WO 97/47632, Examples 28–31).

A preferred embodiment of the present invention is a process which comprises:

(A) reacting hydrocinnamoyl chloride 2:

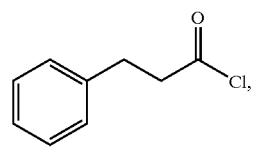

with 2-alkoxypropene and cis-aminoindanol 3:

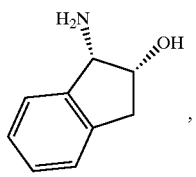

in the presence of inorganic base and an ether as solvent, the reaction mixture having a single liquid phase, to form acetonide 1:

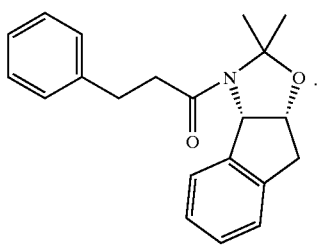

Aspects of this embodiment include Step A as just described wherein:

(a-i) the inorganic base is NaHCO₃ (e.g., anhydrous NaHCO₃);

(a-ii) the inorganic base is LiOH (e.g., anhydrous LiOH);

(a-iii) the solvent is tetrahydrofuran;

(a-iv) the 2-alkoxypropene is 2-methoxypropene;

(a-v) the reaction is conducted at a temperature in the range of from about 0 to about 80° C.;

(a-vi) hydrocinnamyl chloride 2 is employed in an amount of from about 1 to about 2 equivalents per equivalent of cis-aminoindanol 3, (a-vii) the 2-alkoxypropene is employed in an amount of from about 3.8 to about 10 equivalents per equivalent of 3;

(a-viii) the base is employed in an amount of from about 0.5 to about 2 equivalents per equivalent of 3;

(a-ix) hydrocinnamyl chloride 2 is gradually added to an agitated mixture containing the base, 2-methoxypropene, cis-aminoindanol 3, and ether solvent; and (a-x) Step A includes the combination of (a-i) or (a-ii) and any one or more of (a-iii) to (a-ix).

Another preferred embodiment of the present invention is the process for preparing acetonide 1 as set forth in the immediately preceding embodiment (and optionally including any of aspects (a-i) to (a-x)), which further comprises (B) reacting acetonide 1 with allyl halide in strong base and in an ether solvent to form allyl acetonide 4:

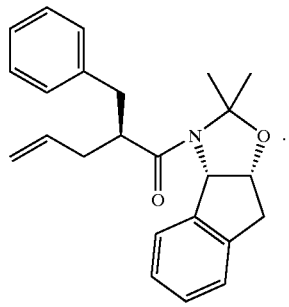

Aspects of this embodiment include Step B as just described wherein:

(b-i) the allyl halide is allyl bromide;

(b-ii) the strong base is lithium hexamethyldisilazide;

(b-iii) the solvent is tetrahydrofuran;

(b-iv) the reaction is conducted at a temperature in the range of from about −78 to about 30° C. (e.g., from about 40 to about −25° C.);

(b-v) the allyl halide is employed in an amount of from about 1 to about 5 equivalents per equivalent of acetonide 1;

(b-vi) the strong base is employed in an amount of from about 1 to about 5 equivalents per equivalent of 1;

(b-vii) the allyl halide is added directly to the Step A reaction mixture containing acetonide 1, followed by addition thereto of the strong base; and (b-viii) Step B includes the combination of any two or more of (b-i) to (b-vii).

The present invention also includes a process for preparing an acetonide of Formula (I):

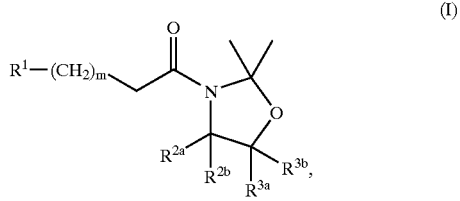

which comprises:

(C) reacting an acid halide of Formula (II):

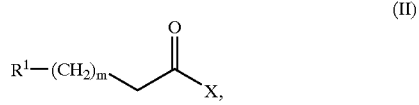

with an aminoalcohol of Formula (III):

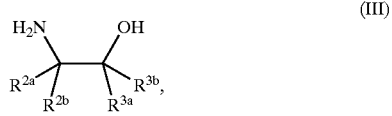

in the presence of LiOH and an ether as solvent, the reaction mixture having a single liquid phase, to form a compound of Formula (V):

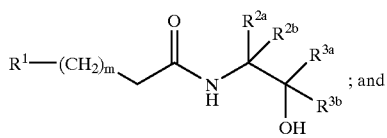

(D) reacting Compound V from Step C with an alkoxy compound which is 2-alkoxypropene or 2,2-dialkoxypropane in the presence of acid and ether solvent to form acetonide I;

wherein $R^1$, $R^{2a}$, $R^{2b}$, $R^{3a}$, $R^{3b}$, and m are as previously defined.

In a preferred embodiment, the 1,2-aminoalcohol is a cis-aminoindanol of Formula (III'):

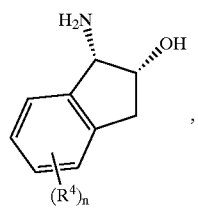

which provides upon reaction in Step C with an acid halide II (as heretofore defined) in the presence of LiOH, a hydroxyamide of Formula (V'):

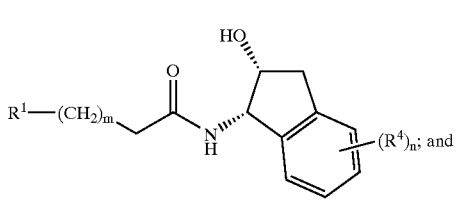

which in turn provides upon reaction in Step D with an alkoxy compound (e.g., 2-alkoxypropene) in the presence of acid, an acetonide of Formula (I'):

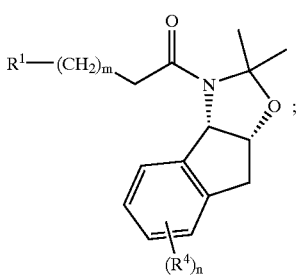

wherein $R^1$, $R^4$, m and n are as previously defined.

Suitable ether solvents for Steps C and D are the same as those set forth above for Step A. The solvents employed in Steps C and D can be the same or different (e.g., by switching the solvent at the conclusion of Step C), but are typically the same. In one embodiment, THF is the solvent in both steps.

The alkoxy compounds for Step D can be the same as those set forth above Step A. In one embodiment, 2-alkoxypropene is employed in Step D. In an aspect of this embodiment, the 2-alkoxypropene is 2-methoxypropene.

The acid in Step D can be a protonic acid or a Lewis acid. Suitable acids include mineral acids such as HCl, sulfuric acid, and nitric acid; Lewis acids such as $BF_3$, $BBr_3$, trimethylsilyltriflate, $AlCl_3$, and $(R^\lambda)_2AlCl$ wherein $R^\lambda$ is $C_1$–$C_6$ alkyl; carboxylic acids such as formic acid, acetic acid, trifluoroacetic acid, and propionic acid); and sulfonic acids such as methanesulfonic acid, ethanesulfonic acid, benzenesulfonic acid, p-toluenesulfonic acid, p-acetamidobenzenesulfonic acid, and dodecylbenzenesulfonic acid). One class of suitable acids are the organic sulfonic acids of formula $R^\wedge$—$SO_2H$, wherein $R^\wedge$ is $C_1$–$C_4$ alkyl. A typically employed acid is methanesulfonic acid.

The reaction temperatures employed in Steps C and D can vary over a wide range, but in each step is suitably in the range of from about 0 to about 80° C., and is typically in the range of from about 40 to about 65° C.

It is normally desired to achieve a maximum conversion of aminoalcohol III and maximum yield of Compound I, and relative proportions of reactants and reagents suitable for this purpose are typically employed, although other proportions affording at least some of the desired product are within the scope of the invention. Acyl halide II is suitably employed in Step C in an amount in the range of from about 1 to about 2 equivalents per equivalent of Compound III, and is typically employed in an amount in the range of from 1 to about 1.2 equivalents per equivalent of III. LiOH is suitably employed in Step C in an amount in the range of from about 0.5 to about 5 equivalents per equivalent of Compound III, and is typically employed in an amount in the range 1.0 to about 1.2 equivalents per equivalent of III.

The alkoxy compound (e.g., a 2-alkoxypropene such as 2-methoxypropene) is suitably employed in Step D in an amount in the range of from about 1.8 to about 10 equivalents per equivalent of aminoalcohol III, and is typically employed in an amount in the range of from about 1.8 to about 2.2 equivalents per equivalent of III. The acid (e.g., methanesulfonic acid) is suitably employed in an amount of from about 0.01 to about 0.5 equivalents per equivalent of aminoalcohol III, and is typically employed in an amount in the range of from about 0.03 to about 0.1 equivalents per equivalent of III.

LiOH, ether solvent, an aminoalcohol M are typically charged to the reaction vessel to form a slurry, followed by slow addition of acid chloride II to the slurry. Dry reagents and reactants are employed, and the reaction mixture is free of moisture at the start of the reaction. For example, the reaction mixture can have a KF of less than about 3000 mg per liter at the start of the reaction. The slurry is typically agitated (e.g., stirred) during its formation and during the acid chloride addition. The addition of Compound II is exothermic, so that suitable temperature control is required. When addition of Compound II is complete, the dry mixture is brought to reaction temperature for a time sufficient to form hydroxyamide V (alternatively referred to herein as "ageing" the reaction batch). The by-product water from hydroxyamide formation is typically removed from the Step C reaction mixture (e.g., by azeotropic distillation), after which Step D is typically commenced by addition of the 2-alkoxypropene or 2,2-dialkoxypropane, followed by addition of the acid. The by-product water need not be removed before commencement of Step D. As an alternative, Step D can be conducted with a sufficient excess of alkoxy compound (e.g., 2-alkoxypropene) which will be hydrolyzed, thereby minimizing the amount of water present in the Step D mixture (e.g., the reaction of the by-product water with 2-alkoxypropene will result in acetone and alkanol). This approach, however, is not preferred, because it involves the unproductive consumption of alkoxy compound (e.g., 2-alkoxypropene). For both Steps C and D, the reaction mixture is typically agitated throughout the reaction.

The reaction mixture in Step C can be characterized as having a single liquid phase under the Step C reaction conditions, wherein the mixture forms a predominantly organic, single liquid phase that contains all of the reaction components (including the LiOH base and its Li halide by-product) in solution. The reaction mixture can also be characterized as homogeneous.

The progress of the reaction in Steps C and D can be followed by monitoring the disappearance of a reactant (e.g., Compound III) and/or the appearance of product I using an analytical technique such as TLC, HPLC, NMR or GC. At the conclusion of the reaction, acetonide I can be recovered from the Step D reaction mixture by conventional means. Compound I can, for example, be recovered in the same manner set forth above for recovery of Compound I from the Step A reaction mixture. However, when acetonide I is to undergo allylation (Step E below), it is typically not recovered. In analogy with the Step A reaction mixture, the Step D reaction mixture, with suitable work-up (e.g., addition of LiOH to quench the acid), is typically employed directly in the allylation. A key advantage to direct use of the Step D reaction mixture in the Step E allylation is the presence therein of Li halide which has unexpectedly been found to enhance the stereoselectivity of the allyl product.

The present invention also includes the process which comprises Steps C and D as just described and allylation Step E, which is (E) reacting the acetonide of Formula (I) with an allylation agent in strong base and in an ether solvent to form an allyl acetonide of Formula (IV).

In a preferred embodiment, allylation Step E affords an allyl acetonide of Formula (IV') by reaction of an acetonide of Formula (I'), prepared in accordance with Steps C and D as already described, with an allylation agent in strong base and in an ether solvent.

Step E is analogous to allylation Step B; i.e., Step E employs the same reagents in the same proportions using the same reaction conditions and procedures as set forth above for Step B.

A preferred embodiment of the present invention is a process which comprises:

(C) reacting hydrocinnamoyl chloride 2:

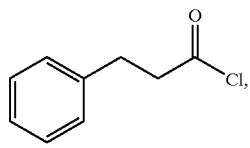

2 with cis-aminoindanol 3:

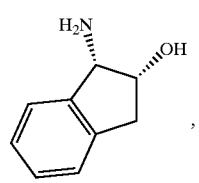

3 in the presence of LiOH and an ether as solvent, the reaction mixture having a single liquid phase, to form hydroxyamide 5:

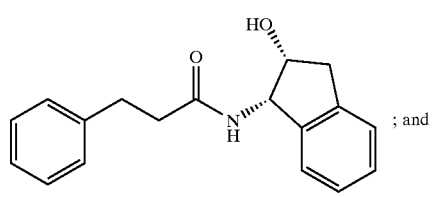

5

; and (D) reacting hydroxyamide 5 from Step C with 2-alkoxypropene in the presence of acid and ether solvent to form acetonide 1:

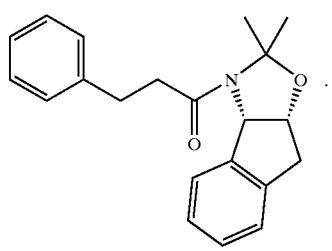

1

Aspects of this embodiment include Steps C and D as just described wherein:

(cd-i) the solvent in both Step C and Step D is tetrahydrofuran;

(cd-ii) the acid in Step D is methanesulfonic acid;

(cd-iii) the 2-alkoxypropene in Step D is 2-methoxypropene;

(cd-iv) Step C is conducted at a temperature in the range of from about 0 to about 80° C.;

(cd-v) Step D is conducted at a temperature in the range of from about 0 to about 80° C.;

(cd-vi) in Step, C hydrocinnamyl chloride 2 is employed in an amount of from about 1 to about 2 equivalents per equivalent of cis-aminoindanol 3;

(cd-vi) in Step C, LiOH (e.g., anhydrous LiOH) is employed in an amount of from about 0.5 to about 5 equivalents per equivalent of compound 3;

(cd-vii) in Step D, 2-alkoxypropene is employed in an amount in the range of from about 1.8 to about 10 equivalents per equivalent of cis-aminoindanol 3;

(cd-viii) in Step D, the acid is employed in an amount of from about 0.01 to about 0.5 equivalents per equivalent of compound 3;

(cd-ix) in Step C, hydrocinnamyl chloride 2 is gradually added to an agitated mixture containing LiOH, cis-aminoindanol 3, and the ether solvent; and (cd-x) Steps C and D include the combination of any two or more of (cd-i) to (cd-ix).

Another preferred embodiment of the present invention is the process for preparing acetonide 1 as set forth in the immediately preceding embodiment (and optionally including any of aspects (cd-i) to (cd-x)), which further comprises (E) reacting acetonide 1 with allyl halide in strong base and in an ether solvent to form allyl acetonide 4.

Aspects of this embodiment include Step E as just described wherein:

(e-i) the allyl halide is allyl bromide;

(e-ii) the strong base is lithium hexamethyldisilazide;

(e-iii) and the solvent is tetrahydrofuran;

(e-iv) the reaction is conducted at a temperature in the range of from about −78 to about 30° C. (e.g., from about −40 to about −25° C.);

(e-v) the allyl halide is employed in an amount of from about 1 to about 5 equivalents per equivalent of acetonide 1;

(e-vi) the strong base is employed in an amount of from about 1 to about 5 equivalents per equivalent of 1;

(e-vii) the allyl halide is added directly to the Step D reaction mixture containing acetonide 1, followed by addition thereto of the strong base; and (e-viii) Step E includes the combination of any two or more of (e-i) to (e-vii).

The present invention also includes a process for preparing an allyl acetonide of Formula (IV'), which comprises reacting an acetonide of Formula (I') with an allylating agent in an ether solvent and in the presence of a lithium salt to form an allyl acetonide of Formula (IV'). The presence of a lithium salt has unexpectedly been found to enhance the stereoselectivity of the allylation. The allylating agent can be any of the agents set forth above in Step B, and is typically an allyl halide (e.g., allyl bromide). Exemplary lithium salts include lithium nitrate, sulfate, perchlorate, halide, and trifluoroacetate. The lithium salt is typically a lithium halide such as LiBr or LiCl. In a preferred embodiment of this process, the allylating agent is allyl bromide and the lithium salt is lithium halide. In another preferred embodiment of this process, the acetonide of Formula (I') is acetonide 1, and the resulting allyl acetonide of Formula (IV') is allyl acetonide 4.

This allylation is analogous to Step B above, and employs the same reagents in the same proportions using the same reaction conditions and procedures as set forth above for Step B. The lithium salt (e.g., LiCl) is suitably present in an amount of from about 0.1 to about 4.0 equivalents per equivalent of acetonide I', and is typically present in an amount of from about 0.8 to about 1.2 equivalents per equivalent of acetonide I'. The lithium salt can be charged as a solid to the reaction vessel prior to the allylation. When a lithium halide is employed, the lithium halide can alternatively be charged in an ether solution with acetonide I', which solution can be prepared in the manner set forth under the description of Step A or of Steps C and D.

As used herein, the term "$C_1$–$C_6$ alkyl" (which may alternatively be referred to herein as "$C_{1-6}$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_1$–$C_4$ alkyl" means n-, iso-, sec- and t-butyl, n- and isopropyl, ethyl and methyl. Similar terms (e.g., "$C_1$–$C_3$ alkyl") have analogous definitions.

The term "$C_1$–$C_6$ alkoxy" means an -O-alkyl group wherein alkyl is $C_1$ to $C_6$ alkyl as defined above. "$C_1$–$C_4$ alkoxy" has an analogous meaning; i.e., it is an alkoxy group selected from methoxy, ethoxy, n-propoxy, isopropoxy, n-butoxy, isobutoxy, tert-butoxy, and sec-butoxy. Similar terms (e.g., "$C_1$–$C_3$ alkoxy") have analogous definitions.

The term "halogen" (which may alternatively be referred to as "halo") refers to fluorine, chlorine, bromine and iodine (alternatively, fluoro, chloro, bromo, and iodo).

The term "halogenated $C_1$–$C_6$ alkyl" (which may alternatively be referred to as "$C_1$–$C_6$ haloalkyl" or "$C_{1-6}$ haloalkyl") means a $C_1$ to $C_6$ linear or branched alkyl group as defined above with one or more halogen substituents. The terms "halogenated $C_1$–$C_4$ alkyl" and "halogenated $C_1$–$C_3$ alkyl" have analogous meanings. The term "fluorinated $C_1$–$C_6$ alkyl" (or "$C_1$–$C_6$ fluoroalkyl" or "$C_{1-6}$ fluoroalkyl") means a $C_1$ to $C_6$ linear or branched alkyl group as defined above with one or more fluorine substituents. The terms "fluorinated $C_1$–$C_4$ alkyl" and "fluorinated $C_1$–$C_3$ alkyl" have analogous meanings. Representative examples of suitable fluoroalkyls include the series $(CH_2)_{0-3}CF_3$ and $(CH_2)_{0-2}CF_3$ (i.e., trifluoromethyl, 2,2,2-trifluoroethyl, and 3,3,3-trifluoro-n-propyl), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "halogenated $C_1$–$C_6$ alkoxy" (which may alternatively be referred to as "$C_1$–$C_6$ haloalkoxy" or "$C_{1-6}$ haloalkoxy") means a $C_1$ to $C_6$ linear or branched alkoxy group as defined above wherein the alkyl group has one or more halogen substituents. The terms "halogenated $C_1$–$C_4$ alkoxy" and "halogenated $C_1$–$C_3$ alkoxy" have analogous meanings. The term "fluorinated $C_1$–$C_6$ alkoxy" (which may alternatively be referred to as "$C_1$–$C_6$ fluoroalkoxy") means a $C_1$–$C_6$ alkoxy group as defined above wherein the alkyl moiety has one or more fluorine substituents. The terms "fluorinated $C_1$–$C_4$ alkoxy" and "fluorinated $C_1$–$C_3$ alkoxy" have analogous meanings. Representative examples include the series $O(CH_2)_{0-3}CF_3$ (i.e., trifluoromethoxy, 2,2,2-trifluoroethoxy, 3,3,3-trifluoro-n-propoxy, etc.), 1,1,1,3,3,3-hexafluoroisopropoxy, and so forth.

The term "$C_2$–$C_8$ alkoxyalkyl" means a linear or branched $C_1$–$C_6$ alkyl group as defined above having as a substituent a $C_1$–$C_6$ alkoxy group as defined above, wherein the alkoxyalkyl group has a total of from 2 to 8 carbon atoms. Similarly, "$C_2$–$C_6$ alkoxyalkyl" means a linear or branched $C_1$–$C_5$ alkyl group as defined above having as a substituent a $C_1$–$C_5$ alkoxy group as defined above, wherein the alkoxyalkyl group has a total of from 2 to 6 carbon atoms. "$C_2$–$C_4$ alkoxyalkyl" means a linear or branched $C_1$–$C_3$ alkyl group as defined above having as a substituent a $C_1$–$C_3$ alkoxy group as defined above, wherein the alkoxyalkyl group has a total of from 2 to 4 carbon atoms. Representative examples of suitable alkoxyalkyl groups include, but are not limited to, the $C_1$–$C_6$ alkoxy-substituted methyl groups (methoxymethyl, ethoxymethyl, n-propoxymethyl, isopropoxymethyl, and the butyloxymethyl, pentyloxymethyl, and hexyloxymethyl isomers), and the $C_1$–$C_6$ alkoxy-substituted ethyl groups. Other suitable alkoxyalkyl groups include the series $(CH_2)_{1-6}OCH_3$, $(CH_2)_{1-4}OCH_3$, $(CH_2)_{1-3}OCH_3$, $(CH_2)_{1-6}OCH_2CH_3$, and $(CH_2)_{1-4}OCH_2CH_3$.

The term "carbocyclic" (which may alternatively be referred to as "carbocycle") refers to a saturated or unsaturated monocyclic ring consisting of from 5 to 7 carbon atoms or a saturated or unsaturated bicyclic ring consisting of from 7 to 10 carbon atoms. It is understood that either or both rings of the bicyclic may be saturated or unsaturated. It is also understood that the term "unsaturated" encompasses both partially and completely unsaturated rings. Exemplary carbocyclics include, but are not limited to, cyclopentyl, cyclohexyl, cylcoheptyl, cyclopentenyl, cyclohexenyl, cycloheptenyl, phenyl, naphthyl, tetrahydronaphthyl (tetralin), indenyl, and indanyl.

The term "aryl" refers to aromatic mono- and poly-carbocyclic ring systems, wherein the carbocyclic rings in the polyring systems may be fused or attached to each other via single bonds. Suitable aryl groups include, but are not limited to, phenyl, naphthyl, and biphenylenyl.

The term "heterocyclic" (which may alternatively be referred to as "heterocycle") refers to (i) a 4- to 8-membered, saturated or unsaturated monocyclic ring consisting of carbon atoms and one or more heteroatoms selected from N, O and S or (ii) a 7- to 10-membered bicyclic ring system, either ring of which is saturated or unsaturated, consisting of carbon atoms and one or more heteroatoms selected from N, O and S; and wherein the nitrogen and sulfur heteroatoms in (i) or (ii) are optionally oxidized, and the nitrogen heteroatom is optionally quaternized. The heterocyclic ring may be attached at any heteroatom or carbon atom, provided that attachment results in the creation of a stable structure. Representative examples of heterocyclic groups include azetidinyl, piperidinyl, piperazinyl, azepinyl, pyrrolyl, indazolyl, pyrrolidinyl, pyrazolyl, pyrazolidinyl, imidazolyl, imidazolidinyl, imidazolinyl, pyridyl, pyrazinyl, pyrimidinyl, pyridazinyl, oxazolyl, oxazolidinyl, triazolyl, isoxazolyl, isoxazolidinyl, morpholinyl, thiazolyl, thiadiazolyl, thiazolidinyl, isothiazolyl, quinoxazolinyl, isothiazolidinyl, methylenedioxyphenyl, quinolinyl, isoquinolinyl, benzimidazolyl, thiadazolyl, benzopyranyl, benzothiazolyl, benzoazolyl, furyl, tetrahydrofuryl, benzofuranyl, benzothiofuranyl, azabenzofuranyl, benzothiazolyl, azabenzothiazolyl, azabenzoxazolyl, tetrahydropuranyl, thiophenyl, thienothiophenyl, benzothiophenyl, and oxadiazolyl.

The term "heteroaryl" refers to a heterocyclic group as defined above, wherein the monocyclic ring (i) is an aromatic ring and at least one ring of the bicyclic ring system (ii) is an aromatic ring. In one aspect, heteroaryl refers to (i) a 5- or 6-membered aromatic ring consisting of carbon atoms and from 1 to 3 heteroatoms selected from N, S, and O or (ii) an 8- to 10-membered bicyclic ring system consisting of carbon atoms and from 1 to 3 heteroatoms selected from N, S, and O, wherein at least one of the rings in the bicyclic system is an aromatic ring.

The term "alkali metal" refers to a metal of Group Ia of the Periodic Table, including but not limited to lithium, sodium, and potassium.

The term "alkaline earth metal" refers to a metal of Group IIa of the Periodic Table, including but not limited to magnesium and calcium.

The term "substituted" (as for example in "$C_1$–$C_6$ alkyl substituted with one or more substituents, each of which is independently . . . ") includes mono- and poly-substitution by a named substituent to the extent such single and multiple substitution is chemically allowed and results in a chemically stable compound.

Abbreviations used in the instant specification include the following:

Ac=acetic or acetate
AIDS=acquired immune deficiency syndrome
ARC=AIDS related complex
Boc=butyloxycarbonyl
DCE=1,2-dichloroethane
DMP=2,2-dimethoxypropane
GC=gas chromatography
HPLC=high performance liquid chromatography
IPAc=isopropyl acetate
KF=Karl Fisher titration for water
LHMDS=lithium hexamethyldisilazide
Me=methyl
MeOH=methanol
MSA=methanesulfonic acid
MTBE=methyl tert-butyl ether
NCS=N-chlorosuccinimide
Ph=phenyl
TCE=1,1,2-trichloroethane
THF=tetrahydrofuran The following examples serve only to illustrate the invention and its practice. The examples are not to be construed as limitations on the scope or spirit of the invention.

EXAMPLE 1

Preparation of (3aS,8aR)-2,2-dimethyl-3-(3-phenylpropanoyl)-3,3a,8,8a-tetrahydro-2H-indeno[1,2-d][1,3]oxazole (Acetonide 1)

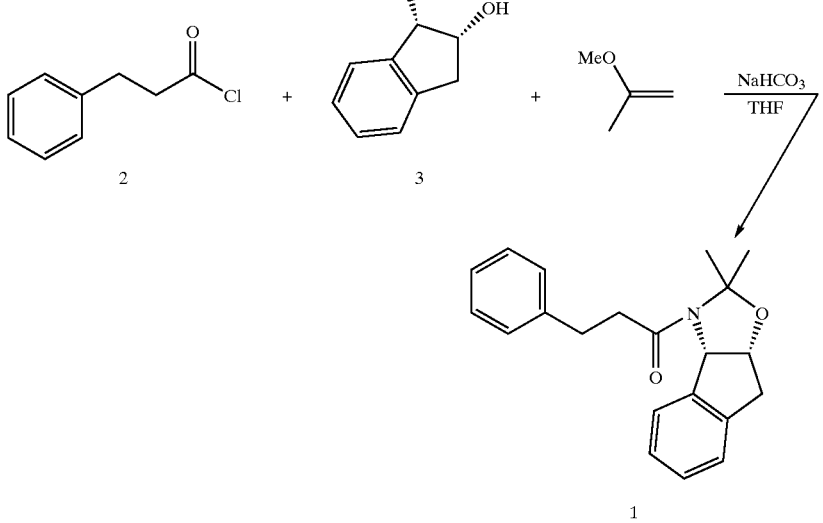

Solid sodium bicarbonate (84.01 g; 1.0 mol; 1.0 equiv.) was added to a 3 neck 5 L Morton flask equipped with mechanical stirrer, thermocouple, condenser, and a nitrogen sweep) followed by dry THF (1.99 L; to give ~75 g/l batch) and solid (−)cis-aminoindan-2-ol (3, 149.19 assay g; 1.0 mol) at 23° C. The resulting slurry was stirred at 300 rpm.

The KF of the solution was measured to be <1100 mg/l. 2-methoxypropene (383.1 ml; 288.47 g; 4.0 mol; 4.0 equiv.) was added subsurfacely. Neat hydrocinnamoyl chloride (2, 153.02 ml; 170.31 g; 1.03 mol; 1.03 equiv.) was then added over one hour. An exotherm occured (5–10° C.) during the addition of 2, and the mixture became a thick, white slurry which dissolved following completion of the addition of 2. The temperature was increased to 40° C. and the batch aged until >99% conversion (as measured by HPLC assay) to acetonide 1 was achieved. Additional sodium bicarbonate (25.2 g; 0.3 mol, 0.3 equiv.) was added to quench excess HCl by-product. The residual HCl was determined by titration to be less than 0.005 mmol. The batch was then concentrated to ~25% of the batch volume (0.70 L) at atmospheric pressure between 45–67° C. and flushed with 2 pot volumes of dry THF (1.4 L) at constant volume between 67–80° C. The temperature was maintained at >74° C. in order to eliminate by evaporation the DMP by-product in the batch. The batch was then diluted with dry THF (0.7 L) to give a 0.72M solution. DMP content was <0.5 area % following dilution via GC analysis. The KF of the batch was less than 180 μg/mL. The solution yield (i.e., the amount of acetonide 1 in the solution as determined by HPLC) was 98%.

$^1$H NMR (300.13 MHz, CDCl$_3$): δ7.36–7.14 (m, 9H), 5.03 (d, J=4.4, 1H), 4.66 (m, 1H), 3.15 (m, 2H), 3.06 (br s, 2H), 2.97 (m, 2H), 1.62 (s, 3H), 1.37 (s, 3H); $^{13}$C NMR (75.5 MHz, CDCl$_3$): δ168.8, 140.9, 140.8, 140.6, 128.6, 128.5, 128.4, 127.1, 126.3, 125.8, 124.1, 96.5, 78.6, 65.9, 38.4, 36.2, 31.9, 26.5, 24.1.

EXAMPLE 2

Preparation of (3aS,8aR)-2,2-dimethyl-3-(3-phenylpropanoyl)-3,3a,8,8a-tetrahydro-2H-indeno[1,2-d][1,3]oxazole (Acetonide 1)

Solid lithium hydroxide (anhydrous) (21.55 g, 0.9 mole, 0.9 equiv.) was added to a 3-neck Morton flask equipped with a mechanical stirrer, condenser, thermocouple and nitrogen. Solid (−)-cis-aminoindan-2-ol (3, 149.19 g, 1.0 mole) was then added, followed by dry THF (1.492 L, to give ~100 g/l batch) at 20° C. The resulting slurry was stirred at 350 RPM. The KF of the solution was <1200 mg/l. 2-Methoxypropene (383.1 ml, 288.47 g, 4.0 mole, 4.0 equiv.) was then added subsurfacely. The flask was then placed in a 20° C. water bath, and neat hydrocinnamoyl chloride (2, 153.02 ml, 173.68 g, 1.03 mole, 1.03 equiv.) was added over 1.25 hours. At about 50% hydrocinnamoyl chloride addition, the solution became clear. At about 90% addition an exotherm occured (5–10° C.). Upon completion of the addition of 2 the batch was warmed to 40° C. and aged until >99.0% conversion (as measured by HPLC assay) to acetonide 1 was achieved. Additional lithium hydroxide (5.99 g, 0.25 mole, 0.25 eq.) was added to the batch to quench excess HCl by-product. The batch was stirred for one hour. Upon quench the batch turned from clear to golden in appearance. Residual HCl was determined by titration to be less than 0.005 mmol. The solution yield was 98%.

EXAMPLE 3

Preparation of (3aS,8aR)-2,2-dimethyl-3-(3-phenylpropanoyl)-3,3a,8,8a-tetrahydro-2H-indeno[1,2-d][1,3]oxazole (Acetonide 1)

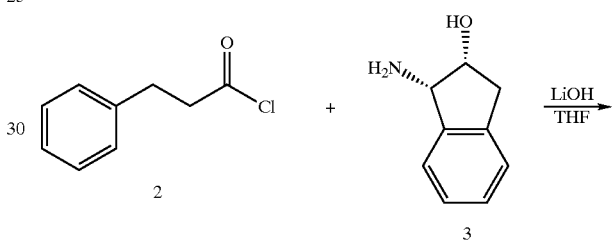

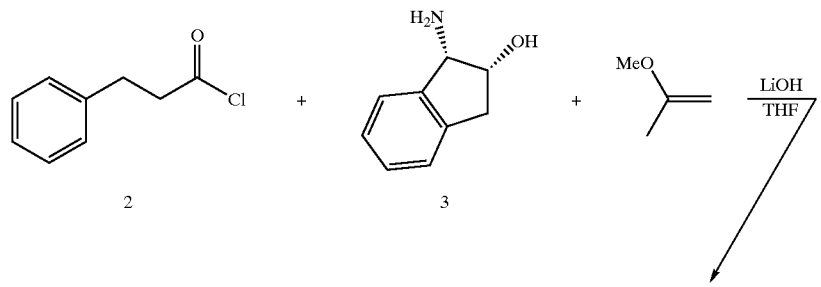

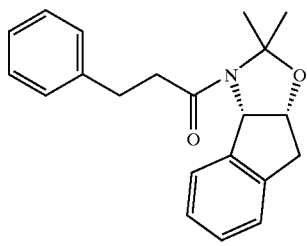

31
-continued

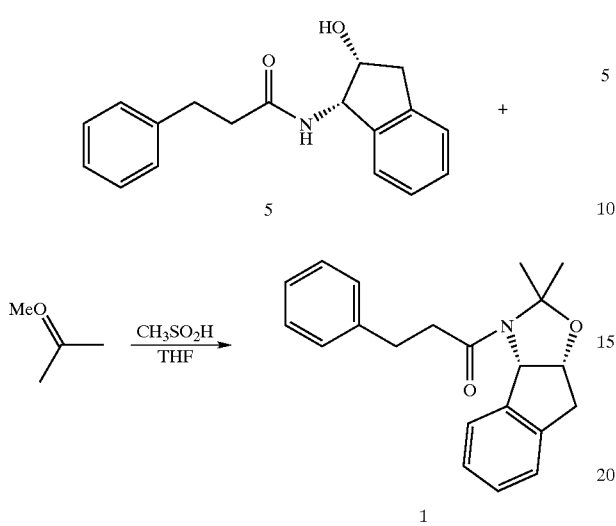

32
EXAMPLE 4

Preparation of (3aS,8aR)-2,2-dimethyl-3-[(2S) 2-phenylmethyl)-4-pentenoyl]-3,3a,8,8a-tetrahydro-2H-indeno[1,2-d][1,3]oxazole (Allyl Acetonide 4)

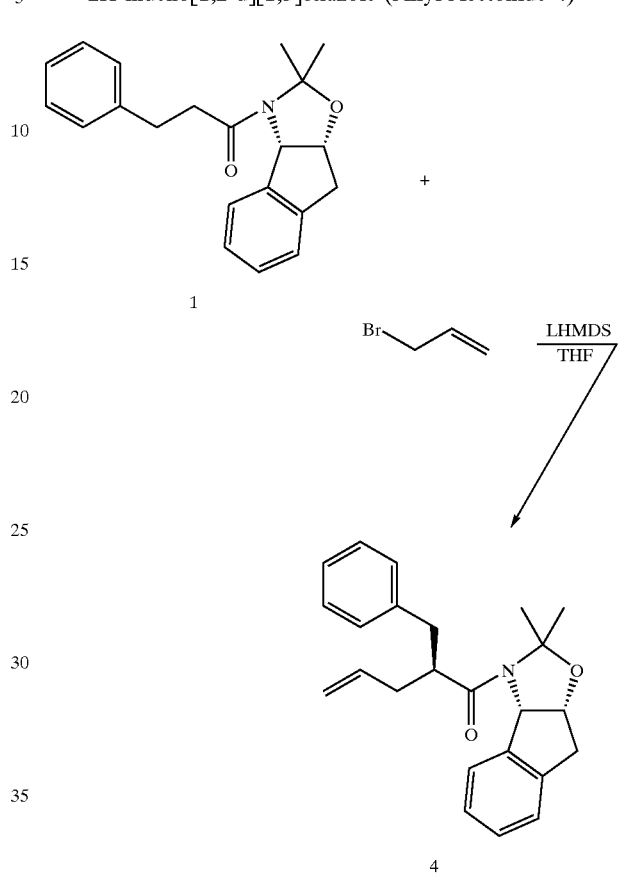

Solid lithium hydroxide (anhydrous) (27.54 g, 1.15 mole, 1.15 eq) was added to a 3 neck 5 L Morton flask equipped with mechanical stirrer, thermocouple and nitrogen sweep, followed by dry THF (1.5 L, to give ~100 g/L batch) and solid (−) cis-aminoindan-2-ol (3, 149.19 g, 1 mole) at 23° C. The mixture (KF<3000 mg/L) was stirred at 400 RPM. Neat hydrocinnamoyl chloride (2, 153.02 ml, 170.31 g, 1.03 mole, 1.03 eq) was added over 1 hour. During the addition the batch cleared up and a 5–10° C. exotherm was observed. The batch was aged at 23° C. for 2 hours with stirring. The pH of the batch was about 9 at this point. The batch was then concentrated to about 25% of the batch volume (0.38 L) at atmospheric pressure between 45–67° C. and flushed with 5 pot volumes of dry THF (1.9 L) at constant volume between 74–80° C. (the temperature was maintained at >74° C. in order to eliminate DMP by-product from the batch by evaporation). The batch was then rediluted with dry THF (1.12 L) to the original volume (batch KF was about 2000 mg/L at this point).

2-Methoxypropene (191.55 ml, 144.24 g, 2.0 mole, 2.0 eq) was then added subsurfacely to the above solution at 20–25° C. under nitrogen. Methanesulfonic acid (5.67 ml, 8.4 g, 0.09 moles, 0.09 eq) was added to the batch and a 10° C. exotherm was observed. The batch was warmed to 40° C. and aged until >99% conversion (as measured by HPLC) to acetonide 1 was achieved. The batch was cooled to 25° C. and lithium hydroxide anhydrous (3.58 g, 0.15 moles 0.15 eq) was added. The batch was stirred for 1 hour and titrated for excess acid. The batch was then concentrated to 25% of the of the original volume (0.38 L) and flushed with 1 pot volume (0.38 L) of dry THF at constant volume. The batch was then diluted with dry THF (0.79 L) to give a 0.72 M solution. The DMP level in the solution was less than 0.5 area % (HPLC) and the KF was less than 200 μg/mL. The solution yield was 98%.

Allyl bromide (96 ml; 134.29 g; 1.11 mol; 1.11 equiv.) was added to the acetonide/THF mixture prepared in Example 3 and the temperature was decreased to −30° C. LHMDS/THF (calculated based on wt %; 1.06 mol; 1.06 equiv.) was added to the solution while maintaining the temperature <−25° C. The mixture was aged at ≦−25° C. until HPLC analysis showed >99.0% conversion. The mixture was quenched with 18 w/w % citric acid (57.64 g; 0.3 mol; 0.3 equiv.) in dry THF (295 ml; 263 g). The temperature of the mixture rose to approximately −10° C. and was stirred for 45 minutes. The mixture was then concentrated in vacuo at 26–27 in. Hg to ~35% of the original volume (0.63 L) while keeping the temperature between 23–30° C. at ~27 in Hg. The mixture was solvent switched to IPAc in vacuo with ~2 pot volumes of IPAc (1.26 L) as a continuous feed between 30–35° C. and the mixture was diluted with IPAc (1.59 L) to give a 0.35 M solution. The solvent switch was stopped when GC analysis indicated that <1 volume percent THF remained. The resulting allyl acetonide/IPAc layer was washed with water (2.0 L), 0.3M sulfuric acid (34.5 mL in 2.04 L water), and 6 w/w % sodium bicarbonate (114.25 g; 1.36 mol; 1.36 equiv. in 1.79 L water). The product (2S)-allyl acetonide 4 was obtained in 93% yield and 93.2% de, as determined by HPLC assay. ("de"="diastermeomeric excess"; %de=100×[(2S−2R)/(2S+2R)]. m.p. 101–102° C.

$^{13}$C NMR (62.9 Mhz, CDCl3) δ171.0, 140.4, 140.2, 134.8, 129.6, 128.6, 128.2, 127.1, 126.6, 125.6, 124.0, 117.9, 96.8, 78.9, 65.6, 47.5, 38.6, 38.0, 36.1, 26.6, 24.1. FTIR (thin film) $v_{max}$ 2926, 1645, 1420 cm$^{-1}$.

The allyl acetonide 4 solution in IPAc can be used directly in the preparation of Compound J (indinavir) as set forth in Examples 28–31 of International Publication No. WO 97/47632.

EXAMPLE 5

Preparation of (3aS,8aR)-2,2-dimethyl-3-[(2S) 2-phenylmethyl)-4-pentenoyl]-3,3a,8,8a-tetrahydro-2H-indeno[1,2-d][1,3]oxazole (Allyl Acetonide 4)

A series of allyl acetonide 4 solutions in IPAc were prepared using the procedure described in Example 4. The reaction conditions and parameters were substantially the same, except that here the ageing temperature was maintained at a constant −25° C. The diastereoselectivities of the resulting allyl acetonides are shown in the Table below. The results show that the presence of LiCl enhances the diastereoselectivity of 4.

| Source of Acetonide 1 | Diastereomieric Excess (%) |
|---|---|
| Ex. 2 - LiOH | 93.3 |
| Ex. 2 - LiOH | 93.2 |
| Ex. 1 - NaHCO$_3$ | 92.8 |
| Ex. 1 - NaHCO$_3$ | 92.8 |
| Ex. 1 - NaHCO$_3$ | 92.8 |
| Ex. 1 - NaHCO$_3$ + LiCl (1 eq.) | 93.6 |
| Ex. 1 - NaHCO$_3$ + LiCl (1 eq.) | 93.6 |
| Ex. 1 - NaHCO$_3$ + LiCl (1 eq.) | 93.6 |

"Ex.2 - LiOH" denotes that the acetonide 1/THF solution used in the allylation was prepared in accordance with the procedure of Example 2, using LiOH as the base. LiCl is present as a by-product in the acetonide 1/THF solution.
"Ex. 1 - NaHCO$_3$" denotes that the acetonide 1/THF solution was prepared in accordance with the procedure of Example 1, using NaHCO$_3$ as the base.
"Ex. 1 - NaHCO$_3$ + LiCl (1 eq.)" denotes that the acetonide 1/THF solution was prepared in accordance with the procedure of Example 1, using NaHCO$_3$ as the base, and that 1 equivalent of LiCl was added to the acetonide/THF solution prior to the allylation.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A process for preparing an acetonide of Formula (I):

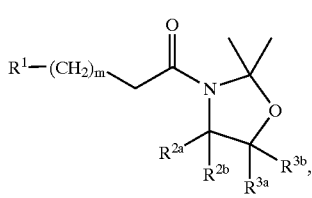

(I)

which comprises:

(A) reacting an acid halide of Formula (II):

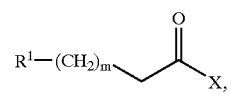

(II)

with an alkoxy compound which is 2-alkoxypropene or 2,2-dialkoxypropane and an aminoalcohol of Formula (III):

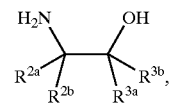

(III)

in the presence of LiOH and an ether as solvent, the reaction mixture having a single liquid phase, to form Compound I; wherein
$R^1$ is
(1) hydrogen;
(2) $C_1$–$C_6$ alkyl;
(3) $C_1$–$C_6$ alkyl substituted with one or more substituents, each of which is independently hydroxy, cyano, or halo;
(4) $C_3$–$C_8$ cycloalkyl;
(5) $C_3$–$C_8$ cycloalkyl substituted with one or more substituents, each of which is independently $C_1$–$C_4$ alkyl, hydroxy, cyano, or halo;
(6) aryl;
(7) aryl substituted with one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —CO$_2$R$^a$, —COR$^a$, NR$^a$R$^b$, —NR$^a$—COR$^b$, —NR$^b$—CO$_2$R$^b$, —CO—NR$^a$R$^b$, —OCO—NR$^a$R$^b$, —NR$^a$CO—NR$^a$R$^b$, —S(O)$_k$R$^a$ wherein k is an integer from 0 to 2, —S(O)$_2$—NR$^a$R$^b$, —NR$^a$S(O)$_2$—R$^b$, or —NR$^a$S(O)$_2$—NR$^a$R$^b$;
(8) heterocycle; or
(9) heterocycle substituted one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —CO$_2$R$^a$, —COR$^a$, —NR$^a$R$^b$, —NR$^a$—COR$^b$, —NR$^b$—CO$_2$R$^b$, —CO—NR$^a$R$^b$, —OCO—NR$^a$R$^b$, —NR$^a$CO—NR$^a$R$^b$, —S(O)$_k$R$^a$ wherein k is an integer from 0 to 2, —S(O)$_2$—NR$^a$R$^b$, —NR$^a$S(O)$_2$—R$^b$, or —NR$^a$S(O)$_2$—NR$^a$R$^b$;
$R^{2a}$, $R^{2b}$, $R^{3a}$ and $R^{3b}$ each independently have the same definition as $R^1$; or
$R^{2a}$ and $R^{3a}$ each independently have the same definition as $R^1$, and $R^{2b}$ and $R^{3b}$ together with the carbon atoms to which each is attached form
(1) a carbocycle;
(2) a carbocycle substituted with one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —CO$_2$R$^a$, —COR$^a$, —NR$^a$R$^b$, —NR$^a$—COR$^b$, —NR$^b$—CO$_2$R$^b$, —CO—NR$^a$R$^b$, —OCO—NR$^a$R$^b$, —NR$^a$CO—NR$^a$R$^b$, —S(O)$_k$R$^a$ wherein k is an integer from 0 to 2, —S(O)$_2$—NR$^a$R$^b$, —NR$^a$S(O)$_2$—R$^b$, or —NR$^a$S(O)$_2$—NR$^a$R$^b$;
(3) a heterocycle; or
(4) a heterocycle substituted with one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^a$CO—$NR^aR^b$, —$S(O)_kR^a$ wherein k is an integer from 0 to 2, —$S(O)_2$—$NR^aR^b$, —$NR^aS(O)_2$—$R^b$, or —$NR^aS(O)_2$—$NR^aR^b$;

each $R^a$ and $R^b$ is independently hydrogen or $C_1$–$C_4$ alkyl;

X is halogen; and m is an integer from 0 to 5;

wherein the carbocycle is a saturated or unsaturated monocyclic ring consisting of from 5 to 7 carbon atoms or a bicyclic ring consisting of from 7 to 10 carbon atoms in which either or both rings of the bicyclic are saturated or unsaturated;

the aryl is an aromatic mono- and poly-carbocyclic ring system wherein the carbocyclic rings in the polyring system are either fused or attached to each other via single bonds; and each heterocycle is independently a (i) a 4- to 8-membered, saturated or unsaturated monocyclic ring consisting of carbon atoms and one or more heteroatoms selected from N, O and S or (ii) a 7- to 10-membered bicyclic ring system, either ring of which is saturated or unsaturated, consisting of carbon atoms and one or more heteroatoms selected from N, O and S; and wherein the nitrogen and sulfur heteroatoms in (i) or (ii) are optionally oxidized, and the nitrogen heteroatom is optionally quaternized.

2. The process according to claim 1, wherein:

$R^1$ is aryl or substituted aryl; wherein each of the one or more substituents on substituted aryl is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, or —$COR^a$;

$R^{2a}$ and $R^{3a}$ are both hydrogen;

$R^{2b}$ and $R^{3b}$ together with the carbon atoms to which each is attached form carbocycle, substituted carbocycle, heterocycle or substituted heterocycle; wherein each of the one or more substituents on substituted carbocycle or substituted heterocycle is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, or —$COR^a$; and m is an integer from 0 to 2.

3. The process according to claim 1, wherein the solvent is tetrahydrofuran.

4. The process according to claim 1, wherein the reaction is conducted at a temperature in the range of from about 0 to about 80° C.

5. The process according to claim 1, wherein the alkoxy compound is 2-alkoxypropene.

6. The process according to claim 1, wherein acyl halide II is employed in an amount of at least about one equivalent per equivalent of aminoalcohol III, the alkoxy compound is employed in an amount of at least about 1.8 equivalents per equivalent of aminoalcohol III, and the base is employed in an amount of at least about 0.5 equivalents per equivalent of aminoalcohol III.

7. The process according to claim 1, which further comprises:

(B) reacting the acetonide of Formula (I) with an allylation agent in strong base and in an ether solvent to form an allyl acetonide of Formula (IV):

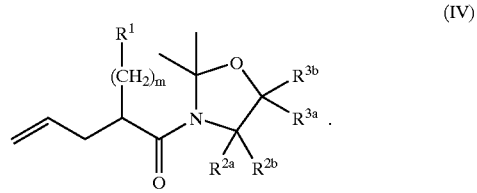

8. A process for preparing an acetonide of Formula (I'):

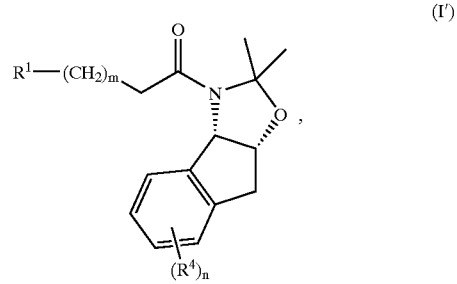

which comprises:

(A) reacting an acid halide of Formula (II):

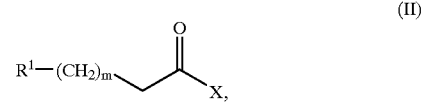

with an alkoxy compound which is 2-alkoxypropene or 2,2-dialkoxypropane and a cis-aminoindanol of Formula (III')

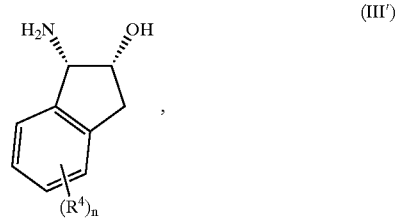

in the presence of LiOH and an ether as solvent, the reaction mixture having a single liquid phase, to form Compound I';

wherein $R^1$ is (1) hydrogen;

(2) $C_1$–$C_6$ alkyl;

(3) $C_1$–$C_6$ alkyl substituted with one or more substituents, each of which is independently hydroxy, cyano, or halo;

(4) $C_3$–$C_8$ cycloalkyl;

(5) $C_3$–$C_8$ cycloalkyl substituted with one or more substituents, each of which is independently $C_1$–$C_4$ alkyl, hydroxy, cyano, or halo;

(6) aryl;

(7) aryl substituted with one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^a$CO—$NR^aR^b$, —$S(O)_kR^a$ wherein k is an integer from 0 to 2, —S(O)$_2$—NR$^a$R$^b$, —NR$^a$S(O)$_2$—R$^b$, or —NR$^a$S(O)$_2$—NR$^a$R$^b$;
(8) heterocycle; or
(9) heterocycle substituted one or more substituents, each of which is independently C$_1$–C$_4$ alkyl, halogenated C$_1$–C$_4$ alkyl, C$_1$–C$_4$ alkoxy, halogenated C$_1$–C$_4$ alkoxy, hydroxy, cyano, halo, phenyl, —CO$_2$R$^a$, —COR$^a$, —NR$^a$R$^b$, —NR$^a$—COR$^b$, —NR$^b$—CO$_2$R$^b$, —CO—NR$^a$R$^b$, —OCO—NR$^a$R$^b$, —NR$^a$CO—NR$^a$R$^b$, —S(O)$_k$R$^a$ wherein k is an integer from 0 to 2, —S(O)$_2$—NR$^a$R$^b$, —NR$^a$S(O)$_2$—R$^b$, or —NR$^a$S(O)$_2$—NR$^a$R$^b$;

each R$^a$ and R$^b$ is independently hydrogen or C$_1$–C$_4$ alkyl;

X is halogen;

m is an integer from 0 to 5;

each R$^4$ is independently
(1) C$_1$–C$_4$ alkyl;
(2) halogenated C$_1$–C$_4$ alkyl;
(3) C$_1$–C$_4$ alkoxy,
(4) halogenated C$_1$–C$_4$ alkoxy
(5) hydroxy,
(6) cyano,
(7) halo,
(8) —CO$_2$R$^c$,
(9) —COR$^c$,
(10) —NR$^c$R$^d$,
(11) —NR$^c$—COR$^d$,
(12) —NR$^c$—CO$_2$R$^d$,
(13) —CO—NR$^c$R$^d$,
(14) —OCO—NR$^c$R$^d$,
(15) —NR$^c$CO—NR$^c$R$^d$,
(16) —S(O)$_k$—R$^c$ wherein k is an integer from 0 to 2,
(17) —S(O)$_2$—NR$^c$R$^d$,
(18) —NR$^c$S(O)$_2$—R$^d$, or
(19) —NR$^c$S(O)$_2$—NR$^c$R$^d$;

each R$^c$ and R$^d$ is independently hydrogen or C$_1$–C$_4$ alkyl; and n is an integer from 0 to 4;

wherein
the aryl is an aromatic mono- and poly-carbocyclic ring system wherein the carbocyclic rings in the polyring system are either fused or attached to each other via single bonds; and
the heterocycle is a (i) a 4- to 8-membered, saturated or unsaturated monocyclic ring consisting of carbon atoms and one or more heteroatoms selected from N, O and S or (ii) a 7- to 10-membered bicyclic ring system, either ring of which is saturated or unsaturated, consisting of carbon atoms and one or more heteroatoms selected from N, O and S; and wherein the nitrogen and sulfur heteroatoms in (i) or (ii) are optionally oxidized, and the nitrogen heteroatom is optionally quaternized.

9. The process according to claim 8, wherein R$^1$ is aryl or substituted aryl; and m is an integer from 0 to 2.

10. The process according to claim 9, wherein R$^1$ is phenyl or substituted phenyl.

11. The process according to claim 8, wherein the solvent is tetrahydrofuran.

12. The process according to claim 8, wherein the reaction is conducted at a temperature in the range of from about 0 to about 80° C.

13. The process according to claim 8, wherein the alkoxy compound is 2-alkoxypropene.

14. The process according to claim 8, wherein acyl halide II is employed in an amount of at least about one equivalent per equivalent of aminoalcohol III', the alkoxy compound is employed in an amount of at least about 1.8 equivalents per equivalent of aminoalcohol III', and the base is employed in an amount of at least about 0.5 equivalents per equivalent of aminoalcohol III'.

15. The process according to claim 8, which further comprises:
(B) reacting the acetonide of Formula (I') with an allylation agent in strong base and in an ether solvent to form an allyl acetonide of Formula (IV'):

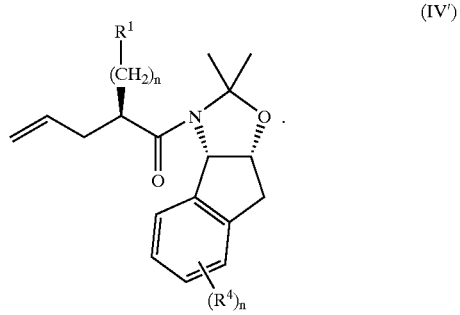

(IV')

16. A process for preparing acetonide 1:

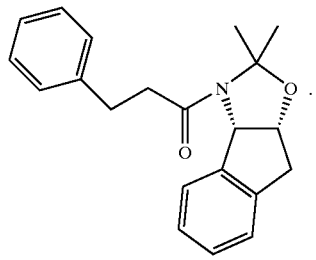

1 which comprises:
(A) reacting hydrocinnamoyl chloride 2:

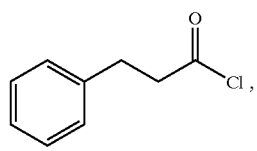

2 with 2-alkoxypropene and cis-aminoindanol 3:

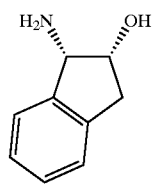

3 in the presence of LiOH and an ether as solvent, the reaction mixture having a single liquid phase, to form acetonide 1.

17. The process according to claim 16, wherein the solvent is tetrahydrofuran.

18. The process according to claim 16, wherein the reaction is conducted at a temperature in the range of from about 0 to about 80° C.

19. The process according to claim 16, wherein the 2-alkoxypropene is 2-methoxypropene.

20. The process according to claim 16, wherein hydrocinnamyl chloride 2 is employed in an amount of from about 1 to about 2 equivalents per equivalent of cis-aminoindanol 3, the 2-alkoxypropene is employed in an amount of at from about 3.8 to about 10 equivalents per equivalent of 3, and the base is employed in an amount of from about 0.5 to about 2 equivalents per equivalent of 3.

21. The process according to claim 16, wherein hydrocinnamyl chloride 2 is gradually added to an agitated mixture containing the base, 2-alkoxypropene, cis-aminoindanol 3, and ether solvent.

22. The process according to claim 16, wherein the ether solvent is tetrahydrofuran;

the 2-alkoxypropene is 2-methoxypropene;

the reaction is conducted at a temperature in the range of from about 0 to about 80° C.;

hydrocinnamyl chloride 2 is employed in an amount of from about 1 to about 2 equivalents per equivalent of cis-aminoindanol 3, the 2-methoxypropene is employed in an amount of at from about 3.8 to about 10 equivalents per equivalent of 3, and LiOH is employed in an amount of from about 0.5 to about 2 equivalents per equivalent of 3; and hydrocinnamyl chloride 2 is gradually added to an agitated mixture containing the LiOH, 2-methoxypropene, cis-aminoindanol 3, and the tetrahydrofuran.

23. The process according to claim 16, which further comprises:

(B) reacting acetonide 1 with allyl halide in strong base and in an ether solvent to form allyl acetonide 4:

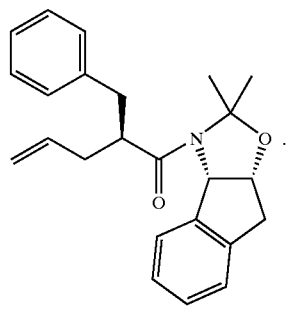

4

24. A process for preparing an acetonide of Formula (I):

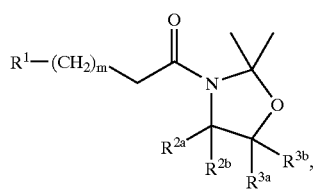

(I)

which comprises:

(C) reacting an acid halide of Formula (II):

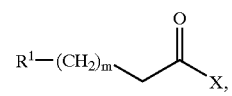

(II)

with an aminoalcohol of Formula (III):

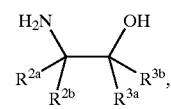

(III)

in the presence of LiOH and an ether as solvent, the reaction mixture having a single liquid phase, to form a compound of Formula (V):

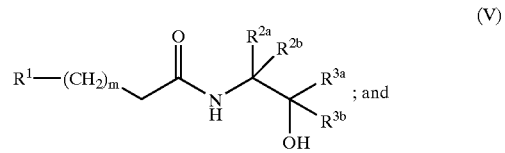

(V)

; and (D) reacting Compound V from Step C with an alkoxy compound which is 2-alkoxypropene or 2,2-dialkoxypropane in the presence of acid and ether solvent to form acetonide I;

wherein $R^1$ is (1) hydrogen;
(2) $C_1$–$C_6$ alkyl;
(3) $C_1$–$C_6$ alkyl substituted with one or more substituents, each of which is independently hydroxy, cyano, or halo;
(4) $C_3$–$C_8$ cycloalkyl;
(5) $C_3$–$C_8$ cycloalkyl substituted with one or more substituents, each of which is independently $C_1$–$C_4$ alkyl, hydroxy, cyano, or halo;
(6) aryl;
(7) aryl substituted with one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^aCO$—$NR^aR^b$, —$S(O)_kR^a$ wherein k is an integer from 0 to 2, —$S(O)_2$—$NR^aR^b$, —$NR^aS(O)_2R^b$, or —$NR^aS(O)_2$—$NR^aR^b$;
(8) heterocycle; or
(9) heterocycle substituted one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^aCO$—$NR^aR^b$, —$S(O)_kR^a$ wherein k is an integer from 0 to 2, —$S(O)_2$—$NR^aR^b$, —$NR^aS(O)_2$—$R^b$, or —$NR^aS(O)_2$—$NR^aR^b$;

$R^{2a}$, $R^{2b}$, $R^{3a}$ and $R^{3b}$ each independently have the same definition as $R^1$; or $R^{2a}$ and $R^{3a}$ each independently have the same definition as $R^1$, and $R^{2b}$ and $R^{3b}$ together with the carbon atoms to which each is attached form (1) a carbocycle;
(2) a carbocycle substituted with one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —$CO$—$NR^aR^b$, —$OCO$—$NR^aR^b$, —$NR^aCO$—$NR^aR^b$, —$S(O)_kR^a$ wherein k is an integer from 0 to 2, —$S(O)_2$—$NR^aR^b$, —$NR^aS(O)_2$—$R^b$, or —$NR^aS(O)_2$—$NR^aR^b$;
(3) a heterocycle; or
(4) a heterocycle substituted with one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —$CO$—$NR^aR^b$, —$OCO$—$NR^aR^b$, —$NR^aCO$—$NR^aR^b$, —$S(O)_kR^a$ wherein k is an integer from 0 to 2, —$S(O)_2$—$NR^aR^b$, —$NR^aS(O)_2$—$R^b$, or —$NR^aS(O)_2$—$NR^aR^b$;

each $R^a$ and $R^b$ is independently hydrogen or $C_1$–$C_4$ alkyl;

X is halogen; and m is an integer from 0 to 5;

wherein the carbocycle is a saturated or unsaturated monocyclic ring consisting of from 5 to 7 carbon atoms or a bicyclic ring consisting of from 7 to 10 carbon atoms in which either or both rings of the bicyclic are saturated or unsaturated;

the aryl is an aromatic mono- and poly-carbocyclic ring system wherein the carbocyclic rings in the polyring system are either fused or attached to each other via single bonds; and each heterocycle is independently a (i) a 4- to 8-membered, saturated or unsaturated monocyclic ring consisting of carbon atoms and one or more heteroatoms selected from N, O and S or (ii) a 7- to 10-membered bicyclic ring system, either ring of which is saturated or unsaturated, consisting of carbon atoms and one or more heteroatoms selected from N, O and S; and wherein the nitrogen and sulfur heteroatoms in (i) or (ii) are optionally oxidized, and the nitrogen heteroatom is optionally quaternized.

25. The process according to claim 24, wherein:

$R^1$ is aryl or substituted aryl; wherein each of the one or more substituents on substituted aryl is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, or —$COR^a$;

$R^{2a}$ and $R^{3a}$ are both hydrogen;

$R^{2b}$ and $R^{3b}$ together with the carbon atoms to which each is attached form carbocycle, substituted carbocycle, heterocycle or substituted heterocycle; wherein each of the one or more substituents on substituted carbocycle or substituted heterocycle is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, or —$COR^a$; and m is an integer from 0 to 2.

26. The process according to claim 24, wherein the solvent employed in Step C and Step D is tetrahydrofuran.

27. The process according to claim 24, wherein Step C is conducted at a temperature in the range of from about 0 to about 80° C., and Step D is conducted at a temperature in the range of from about 0 to about 80° C.

28. The process according to claim 24, wherein the alkoxy compound in Step D is 2-alkoxypropene.

29. The process according to claim 24, wherein in Step C acyl halide II is employed in an amount in the range of from about 1 to about 2 equivalents per equivalent of aminoalcohol III, and LiOH is employed in an amount of from about 0.5 to about 5 equivalents per equivalent of aminoalcohol III;

and wherein in Step D, the alkoxy compound is employed in an amount in the range of from about 1.8 to about 10 equivalents per equivalent of aminoalcohol III, and methanesulfonic acid is employed in an amount of from about 0.01 to about 0.5 equivalents per equivalent of aminoalcohol III.

30. The process according to claim 24, which further comprises:

(E) reacting the acetonide of Formula (I) with an allylation agent in strong base and in an ether solvent to form an allyl acetonide of Formula (IV):

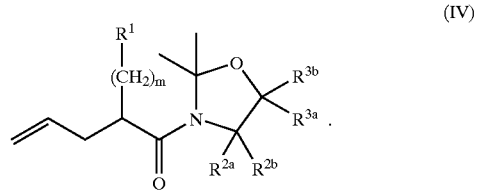

(IV)

31. A process for preparing an acetonide of Formula (I'):

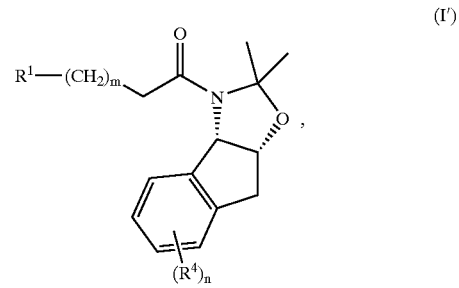

(I')

which comprises:

(C) reacting an acid halide of Formula (II):

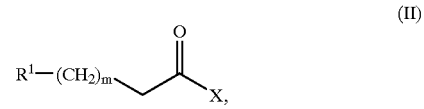

(II)

with a cis-aminoindanol of Formula (III'):

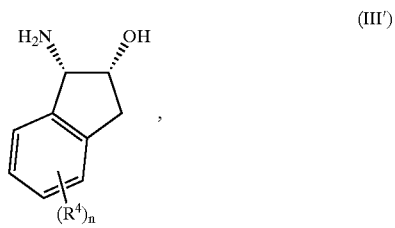

(III')

in the presence of LiOH and an ether as solvent, the reaction mixture having a single liquid phase, to form a compound of Formula (V'):

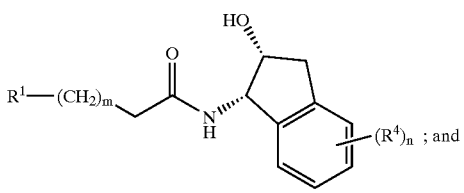

(D) reacting Compound V' from Step C with an alkoxy compound which is 2-alkoxypropene or 2,2-dialkoxypropane in the presence of acid and ether solvent to form acetonide I';

wherein $R^1$ is
- (1) hydrogen;
- (2) $C_1$–$C_6$ alkyl;
- (3) $C_1$–$C_6$ alkyl substituted with one or more substituents, each of which is independently hydroxy, cyano, or halo;
- (4) $C_3$–$C_8$ cycloalkyl;
- (5) $C_3$–$C_8$ cycloalkyl substituted with one or more substituents, each of which is independently $C_1$–$C_4$ alkyl, hydroxy, cyano, or halo;
- (6) aryl;
- (7) aryl substituted with one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^aCO$—$NR^aR^b$, —$S(O)_kR^a$ wherein k is an integer from 0 to 2, —$S(O)_2$—$NR^aR^b$, —$NR^aS(O)_2$—$R^b$, or —$NR^aS(O)_2$—$NR^aR^b$;
- (8) heterocycle; or
- (9) heterocycle substituted one or more substituents, each of which is independently $C_1$–$C_4$ alkyl, halogenated $C_1$–$C_4$ alkyl, $C_1$–$C_4$ alkoxy, halogenated $C_1$–$C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^aCO$—$NR^aR^b$, —$S(O)_kR^a$ wherein k is an integer from 0 to 2, —$S(O)_2$—$NR^aR^b$, —$NR^aS(O)_2$—$R^b$, or —$NR^aS(O)_2$—$NR^aR^b$;

each $R^a$ and $R^b$ is independently hydrogen or $C_1$–$C_4$ alkyl;

X is halogen;

m is an integer from 0 to 5;

each $R^4$ is independently
- (1) $C_1$–$C_4$ alkyl;
- (2) halogenated $C_1$–$C_4$ alkyl;
- (3) $C_1$–$C_4$ alkoxy,
- (4) halogenated $C_1$–$C_4$ alkoxy
- (5) hydroxy,
- (6) cyano,
- (7) halo,
- (8) —$CO_2R^c$,
- (9) —$COR^c$,
- (10) —$NR^cR^d$,
- (11) —$NR^c$—$COR^d$,
- (12) —$NR^c$—$CO_2R^d$,
- (13) —CO—$NR^cR^d$,
- (14) —OCO—$NR^cR^d$,
- (15) —$NR^cCO$—$NR^cR^d$,
- (16) —$S(O)_k$—$R^c$ wherein k is an integer from 0 to 2,
- (17) —$S(O)_2$—$NR^cR^d$,
- (18) —$NR^cS(O)_2$—$R^d$, or
- (19) —$NR^cS(O)_2$—$NR^cR^d$;

each $R^c$ and $R^d$ is independently hydrogen or $C_1$–$C_4$ alkyl; and n is an integer from 0 to 4;

wherein
the aryl is an aromatic mono- and poly-carbocyclic ring system wherein the carbocyclic rings in the polyring system are either fused or attached to each other via single bonds; and the heterocycle is a (i) a 4- to 8-membered, saturated or unsaturated monocyclic ring consisting of carbon atoms and one or more heteroatoms selected from N, O and S or (ii) a 7- to 10-membered bicyclic ring system, either ring of which is saturated or unsaturated, consisting of carbon atoms and one or more heteroatoms selected from N, O and S; and wherein the nitrogen and sulfur heteroatoms in (i) or (ii) are optionally oxidized, and the nitrogen heteroatom is optionally quaternized.

32. The process according to claim 31, wherein $R^1$ is aryl or substituted aryl; and m is an integer from 0 to 2.

33. The process according to claim 32, wherein $R^1$ is phenyl or substituted phenyl.

34. The process according to claim 32, wherein the solvent employed in Step C and Step D is tetrahydrofuran.

35. The process according to claim 32, wherein Step C is conducted at a temperature in the range of from about 0 to about 80° C., and Step D is conducted at a temperature in the range of from about 0 to about 80° C.

36. The process according to claim 32, wherein the alkoxy compound in Step D is 2-alkoxypropene.

37. The process according to claim 32, wherein in Step C acyl halide II is employed in an amount in the range of from about 1 to about 2 equivalents per equivalent of aminoalcohol III, and LiOH is employed in an amount of from about 0.5 to about 5 equivalents per equivalent of aminoalcohol III;

and wherein in Step D, the alkoxy compound is employed in an amount in the range of from about 1.8 to about 10 equivalents per equivalent of aminoalcohol III, and methanesulfonic acid is employed in an amount of from about 0.01 to about 0.5 equivalents per equivalent of aminoalcohol III.

38. The process according to claim 32, which further comprises:

(E) reacting the acetonide of Formula (I') with an allylation agent in strong base and in an ether solvent to form an allyl acetonide of Formula (IV'):

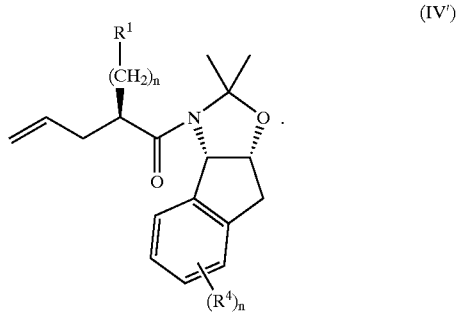

39. A process for preparing acetonide 1:

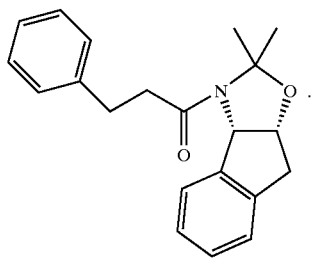

which comprises:

(C) reacting hydrocinnamoyl chloride 2:

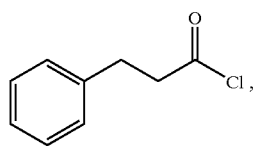

with cis-aminoindanol 3:

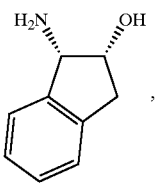

in the presence of LiOH and an ether as solvent, the reaction mixture having a single liquid phase, to form hydroxyamide 5:

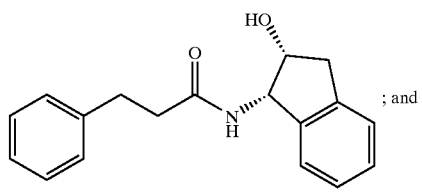
; and (D) reacting hydroxyamide 5 from Step C with 2-alkoxypropene in the presence of acid and ether solvent to form acetonide 1.

40. The process according to claim 39, wherein the solvent in both Step C and Step D is tetrahydrofuran.

41. The process according to claim 39, wherein Step C is conducted at a temperature in the range of from about 0 to about 80° C., and Step D is conducted at a temperature in the range of from about 0 to about 80° C.

42. The process according to claim 39, wherein the 2-alkoxypropene in Step D is 2-methoxypropene.

43. The process according to claim 39, wherein in Step C hydrocinnamyl chloride 2 is employed in an amount of from about 1 to about 2 equivalents per equivalent of cis-aminoindanol 3, and LiOH is employed in an amount of from about 0.5 to about 5 equivalents per equivalent of compound 3; and wherein in Step D, 2-alkoxypropene is employed in an amount in the range of from about 1.8 to about 10 equivalents per equivalent of cis-aminoindanol 3, and the acid is methanesulfonic acid employed in an amount of from about 0.01 to about 0.5 equivalents per equivalent of compound 3.

44. The process according to claim 39, wherein in Step C hydrocinnamyl chloride 2 is gradually added to an agitated mixture containing LiOH, cis-aminoindanol 3, and the ether solvent.

45. The process according to claim 39, wherein the solvent in both Step C and Step D is tetrahydrofuran;

Step C is conducted at a temperature in the range of from about 0 to about 80° C., and Step D is conducted at a temperature in the range of from about 0 to about 80° C.;

in Step C hydrocinnamyl chloride 2 is employed in an amount of from about 1 to about 2 equivalents per equivalent of cis-aminoindanol 3, and LiOH is employed in an amount of from about 0.5 to about 5 equivalents per equivalent of compound 3;

in Step C hydrocinnamyl chloride 2 is gradually added to an agitated mixture containing LiOH, cis-aminoindanol 3, and the tetrahydrofuran; and in Step D, the 2-alkoxypropene is 2-methoxypropene employed in an amount in the range of from about 1.8 to about 10 equivalents per equivalent of cis-aminoindanol 3, and the acid is methanesulfonic acid employed in an amount of from about 0.01 to about 0.1 equivalents per equivalent of compound 3.

46. The process according to claim 39, which further comprises:

(E) reacting acetonide 1 with allyl halide in strong base and in an ether solvent to form allyl acetonide 4:

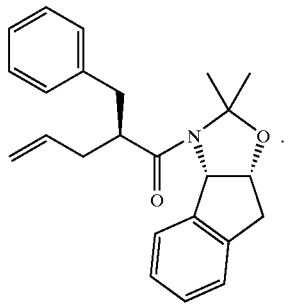

47. A process for preparing an allyl acetonide of Formula (IV'):

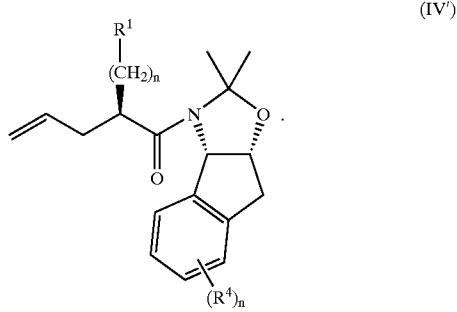

which comprises reacting acetonide of Formula (I'):

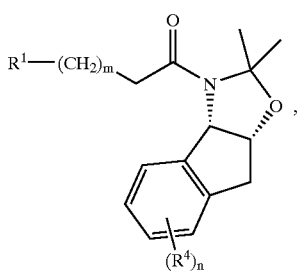

(I')

with allylating agent in strong base, in an ether solvent, and in the presence of a lithium salt;
wherein
  wherein $R^1$ is
  (1) hydrogen;
  (2) $C_1-C_6$ alkyl;
  (3) $C_1-C_6$ alkyl substituted with one or more substituents, each of which is independently hydroxy, cyano, or halo;
  (4) $C_3-C_8$ cycloalkyl;
  (5) $C_3-C_8$ cycloalkyl substituted with one or more substituents, each of which is independently $C_1-C_4$ alkyl, hydroxy, cyano, or halo;
  (6) aryl;
  (7) aryl substituted with one or more substituents, each of which is independently $C_1-C_4$ alkyl, halogenated $C_1-C_4$ alkyl, $C_1-C_4$ alkoxy, halogenated $C_1-C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^aCO$—$NR^aR^b$, —$S(O)_kR^a$ wherein k is an integer from 0 to 2, —$S(O)_2$—$NR^aR^b$, —$NR^aS(O)_2$—$R^b$, or —$NR^aS(O)_2$—$NR^aR^b$;
  (8) heterocycle; or
  (9) heterocycle substituted one or more substituents, each of which is independently $C_1-C_4$ alkyl, halogenated $C_1-C_4$ alkyl, $C_1-C_4$ alkoxy, halogenated $C_1-C_4$ alkoxy, hydroxy, cyano, halo, phenyl, —$CO_2R^a$, —$COR^a$, —$NR^aR^b$, —$NR^a$—$COR^b$, —$NR^b$—$CO_2R^b$, —CO—$NR^aR^b$, —OCO—$NR^aR^b$, —$NR^aCO$—$NR^aR^b$, —$S(O)_kR^a$ wherein k is an integer from 0 to 2, —$S(O)_2$—$NR^aR^b$, —$NR^aS(O)_2$—$R^b$, or —$NR^aS(O)_2$—$NR^aR^b$;
  wherein each $R^4$ is independently
  (1) $C_1-C_4$ alkyl;
  (2) halogenated $C_1-C_4$ alkyl;
  (3) $C_1-C_4$ alkoxy,
  (4) halogenated $C_1-C_4$ alkoxy
  (5) hydroxy,
  (6) cyano,
  (7) halo,
  (8) —$CO_2R^c$,
  (9) —$COR^c$,
  (10) —$NR^cR^d$,
  (11) —$NR^c$—$COR^d$,
  (12) —$NR^c$—$CO_2R^d$,
  (13) —CO—$NR^cR^d$,
  (14) —OCO—$NR^cR^d$,
  (15) —$NR^cCO$—$NR^cR^d$,
  (16) —$S(O)_k$—$R^c$ wherein k is an integer from 0 to 2,
  (17) —$S(O)_2$—$NR^cR^d$,
  (18) —$NR^cS(O)_2$—$R^d$, or
  (19) —$NR^cS(O)_2$—$NR^cR^d$;
each $R^c$ and $R^d$ is independently hydrogen or $C_1-C_4$ alkyl;
m is an integer from 0 to 5; and
n is an integer from 0 to 4;
wherein
  the aryl is an aromatic mono- and poly-carbocyclic ring system wherein the carbocyclic rings in the polyring system are either fused or attached to each other via single bonds; and
  the heterocycle is a (i) a 4- to 8-membered, saturated or unsaturated monocyclic ring consisting of carbon atoms and one or more heteroatoms selected from N, O and S or (ii) a 7- to 10-membered bicyclic ring system, either ring of which is saturated or unsaturated, consisting of carbon atoms and one or more heteroatoms selected from N, O and S; and wherein the nitrogen and sulfur heteroatoms in (i) or (ii) are optionally oxidized, and the nitrogen heteroatom is optionally quaternized.

48. The process according to claim 47, wherein the allylating agent is an allyl halide, and the lithium salt is a lithium halide.

49. A process for preparing an allyl acetonide 4:

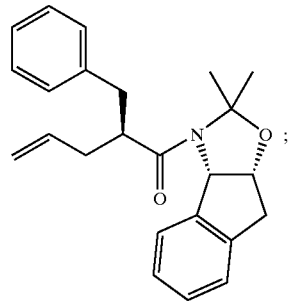

4 which comprises reacting acetonide 1:

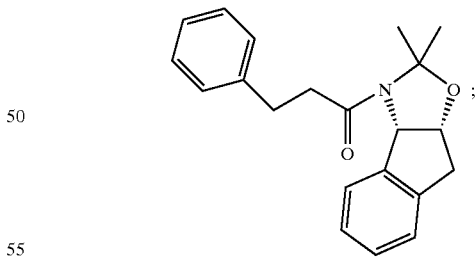

1 with an allyl halide in strong base, in an ether solvent, and in the presence of a lithium halide to obtain 4.

50. The process according to claim 49, wherein the allyl halide is allyl bromide and the lithium salt is LiCl.

* * * * *